United States Patent
Ogata et al.

(10) Patent No.: US 8,918,005 B2
(45) Date of Patent: Dec. 23, 2014

(54) REFLECTION SENSOR AND IMAGE FORMING APPARATUS

(75) Inventors: Kenta Ogata, Kanagawa (JP); Tsutomu Udaka, Kanagawa (JP); Osamu Goto, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 204 days.

(21) Appl. No.: 13/469,160

(22) Filed: May 11, 2012

(65) Prior Publication Data

US 2013/0094875 A1    Apr. 18, 2013

(30) Foreign Application Priority Data

Oct. 12, 2011    (JP) .................... 2011-225088

(51) Int. Cl.
| | |
|---|---|
| G03G 15/00 | (2006.01) |
| G01N 21/55 | (2014.01) |
| H04N 1/00 | (2006.01) |
| G01N 21/17 | (2006.01) |
| G03G 15/01 | (2006.01) |
| H04N 5/335 | (2011.01) |
| H04N 1/047 | (2006.01) |
| H04N 1/50 | (2006.01) |

(52) U.S. Cl.
CPC .. G03G 15/0189 (2013.01); H04N 2201/04732 (2013.01); H04N 1/00023 (2013.01); G03G 15/5054 (2013.01); H04N 1/00055 (2013.01); H04N 1/00045 (2013.01); H04N 1/00031 (2013.01); G03G 2215/0132 (2013.01); G01N 21/17 (2013.01); H04N 2201/04722 (2013.01); H04N 1/00087 (2013.01); G03G 15/01 (2013.01); H04N 1/00013 (2013.01); H04N 1/0009 (2013.01); H04N 2201/04713 (2013.01); H04N 1/0005 (2013.01); H04N 5/335 (2013.01); H04N 1/047 (2013.01); H04N 1/506 (2013.01); H04N 1/00063 (2013.01); H04N 2201/04793 (2013.01)
USPC ................. 399/74; 399/64; 358/1.5; 356/445

(58) Field of Classification Search
USPC ........... 399/49, 64, 74, 301; 358/1.5; 356/445
See application file for complete search history.

(56) References Cited

U.S. PATENT DOCUMENTS 5,157,440 A * 10/1992 Sawayama ...................... 399/74
7,655,936 B2 * 2/2010 Sawayama et al. ........ 250/559.4

(Continued)

FOREIGN PATENT DOCUMENTS

| JP | 5-322760 A | 12/1993 |
|---|---|---|
| JP | 2002-55572 A | 2/2002 |

(Continued)

OTHER PUBLICATIONS

English Translation of Japanese Office Action issued on Jan. 15, 2013 in corresponding Japanese Patent Application No. 2011-225088.

*Primary Examiner* — David Gray
*Assistant Examiner* — Francis Gray
(74) *Attorney, Agent, or Firm* — Sughrue Mion, PLLC

(57) ABSTRACT

A reflection sensor includes the following elements. A light emitting unit emits light to an area of an image forming apparatus where first detection images of plural colors used for detecting amounts of their misregistration are formed. A first light restricting member/configuration restricts light emitted from the light emitting unit. A light receiver is disposed in an optical path of regular reflection light, and receives reflected light and outputs a signal representing an amount of received light. A second light restricting member/configuration is disposed in the optical path of the regular reflection light and restricts light to be received by the light receiver. The value obtained by dividing a diameter of the first light restricting member/configuration by that of the second light restricting member/configuration ranges from substantially 0.5 to 1.9, and the diameters of the first and second light restricting members/configurations are each 1.5 mm or smaller.

5 Claims, 16 Drawing Sheets

(56) References Cited

U.S. PATENT DOCUMENTS

| | | | |
|---|---|---|---|
| 8,565,627 B2 * | 10/2013 | Kinukawa et al. | 399/49 |
| 2002/0051648 A1 | 5/2002 | Shimomura et al. | |
| 2008/0170220 A1 | 7/2008 | Sawayama et al. | |
| 2009/0297191 A1 * | 12/2009 | Hirai et al. | 399/49 |
| 2010/0245921 A1 | 9/2010 | Kikuchi et al. | |

FOREIGN PATENT DOCUMENTS

| | | |
|---|---|---|
| JP | 2002-162803 A | 6/2002 |
| JP | 2004-309292 A | 11/2004 |
| JP | 2010008804 A | 1/2010 |
| JP | 2010-232896 A | 10/2010 |
| JP | 2011-107524 A | 6/2011 |

* cited by examiner

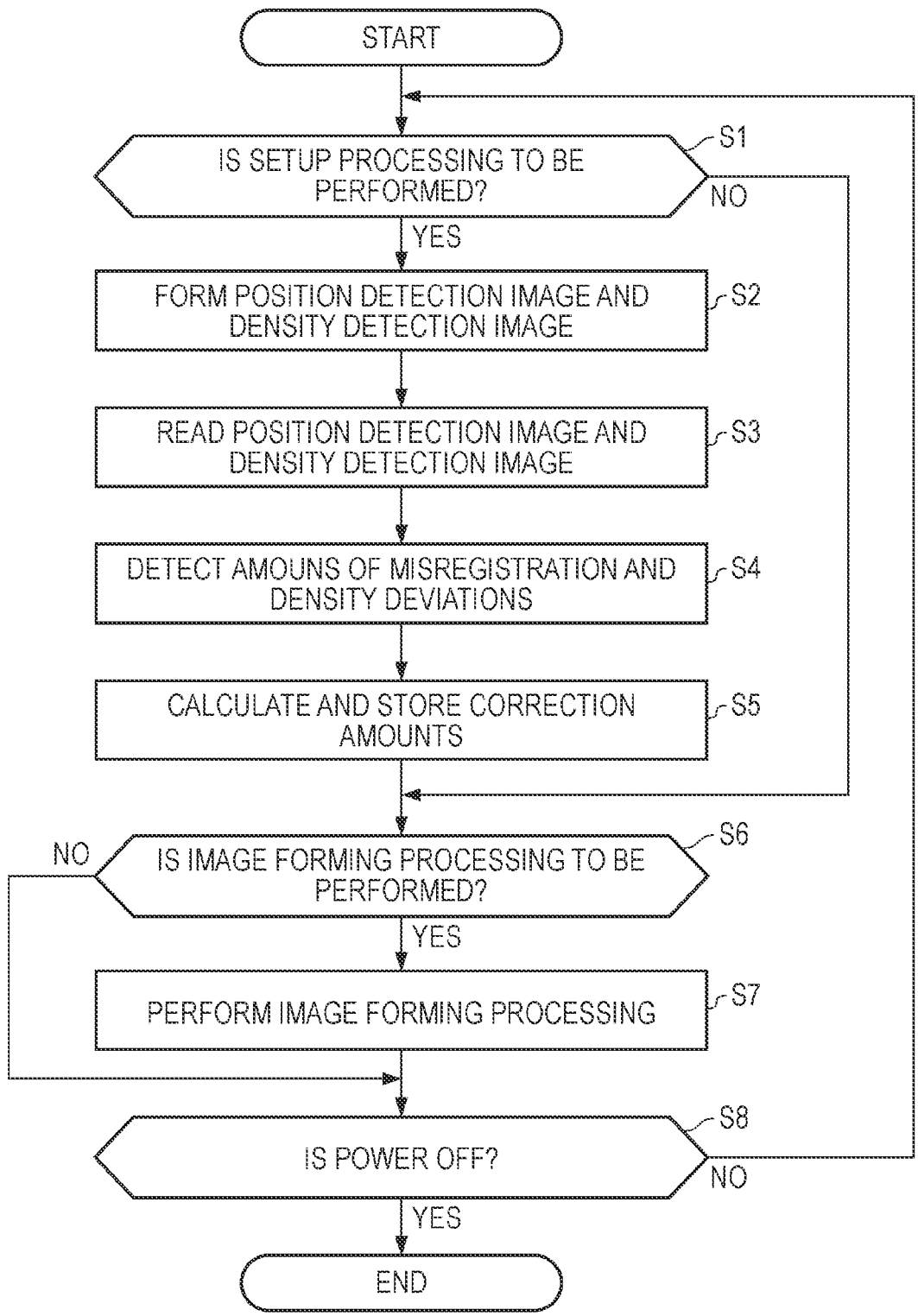

REFLECTION SENSOR AND IMAGE FORMING APPARATUS

CROSS-REFERENCE TO RELATED APPLICATIONS

This application is based on and claims priority under 35 USC 119 from Japanese Patent Application No. 2011-225088 filed Oct. 12, 2011.

BACKGROUND

Technical Field

The present invention relates to a reflection sensor and an image forming apparatus.

SUMMARY

According to an aspect of the invention, there is provided a reflection sensor including: a light emitting unit that emits light to an area of an image forming apparatus where first detection images of plural colors are formed, the first detection images being used for detecting amounts of misregistration among the first detection images; a first light restricting member/configuration that restricts light emitted from the light emitting unit; a light receiver that is disposed in an optical path of regular reflection light generated as a result of light passing through the first light restricting member/configuration and applied to the area being reflected by the area, and that receives light reflected by the area and outputs a signal representing an amount of received light; and a second light restricting member/configuration that is disposed in the optical path of the regular reflection light and that restricts light to be received by the light receiver. A value obtained by dividing a diameter of the first light restricting member/configuration by a diameter of the second light restricting member/configuration ranges from substantially 0.5 to 1.9, and the diameters of the first and second light restricting members/configurations are each 1.5 mm or smaller.

BRIEF DESCRIPTION OF THE DRAWINGS

An exemplary embodiment of the present invention will be described in detail based on the following figures, wherein:

FIG. 8 is a flowchart illustrating process steps executed by a controller of an image forming apparatus;

DETAILED DESCRIPTION

An exemplary embodiment of the present invention will be described below with reference to the accompanying drawings.

Figure 1:
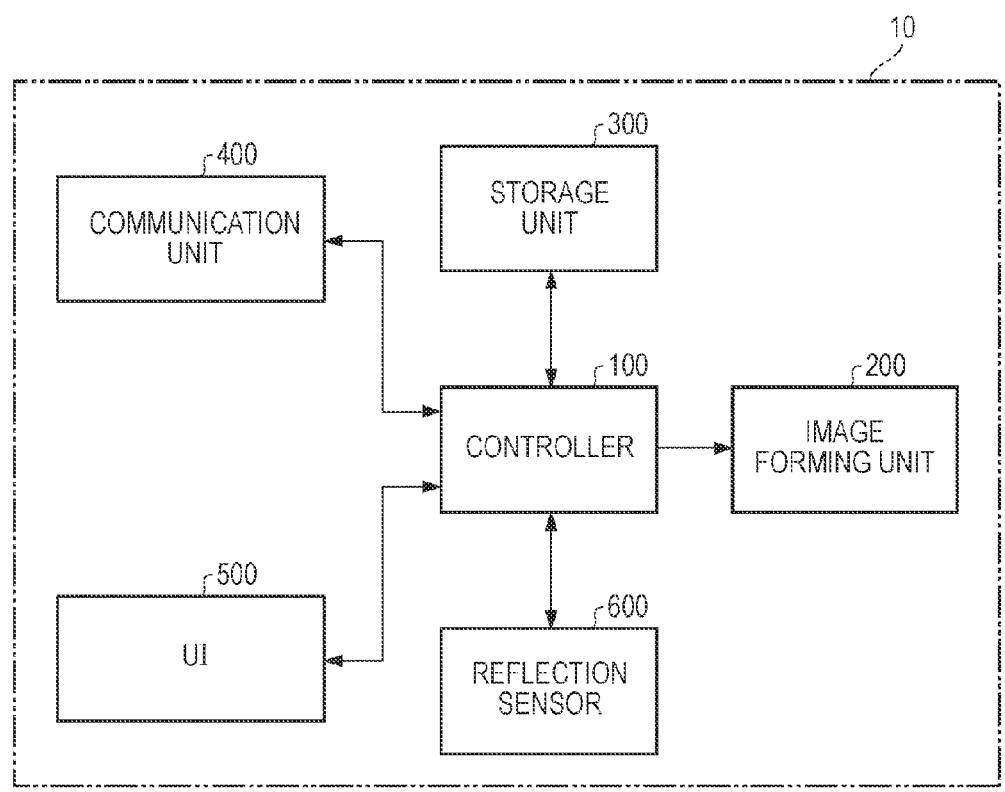
FIG. 1 is a block diagram illustrating an example of the hardware configuration of an image forming apparatus.

FIG. 1 is a block diagram illustrating an example of the hardware configuration of an electrophotographic image forming apparatus 10 according to an exemplary embodiment of the present invention. The electrophotographic image forming apparatus 10 (hereinafter simply referred to as the "image forming apparatus 10") is an example of an image forming apparatus of an exemplary embodiment of the present invention. The image forming apparatus 10 includes, as shown in FIG. 1, a controller 100, an image forming unit 200, a storage unit 300, a communication unit 400, a user interface (UI) 500, and a reflection sensor 600.

The controller 100 includes an arithmetic unit containing a central processing unit (CPU) and an application specific integrated circuit (ASIC), and a memory. The controller 100 controls the individual components of the image forming apparatus 10. The image forming unit 200 is an example of an image forming unit of an exemplary embodiment of the present invention. The image forming unit 200 forms images represented by given image data on a recording medium, such as paper. The image forming unit 200 may be a printer which forms images (more specifically, toner images) through the use of, for example, an electrophotographic process, such as charging, exposure, developing, transfer, fixing, etc. The image forming unit 200 forms images on a recording medium by using four colors of toners, such as yellow (Y), magenta (M), cyan (C), and black (K).

The storage unit 300 includes a storage device, such as a hard disk drive (HDD), and stores therein image data used for image forming processing and image data for forming a position detection image 700a and a density detection image 700b, which will be discussed later, by using the image forming unit 200. The communication unit 400 includes an interface through which the image forming apparatus 10 sends and receives data to and from an external apparatus, and obtains, for example, image data used for forming images. The UI 500 includes, for example, a touch panel, and receives an operation performed by a user and supplies information by displaying images on the touch panel. The reflection sensor 600 is an example of a reflection sensor of an exemplary embodiment of the present invention, and optically reads the surface of an intermediate transfer belt 250, which will be discussed later, of the image forming unit 200, and outputs reading results to the controller 100.

Figure 2:
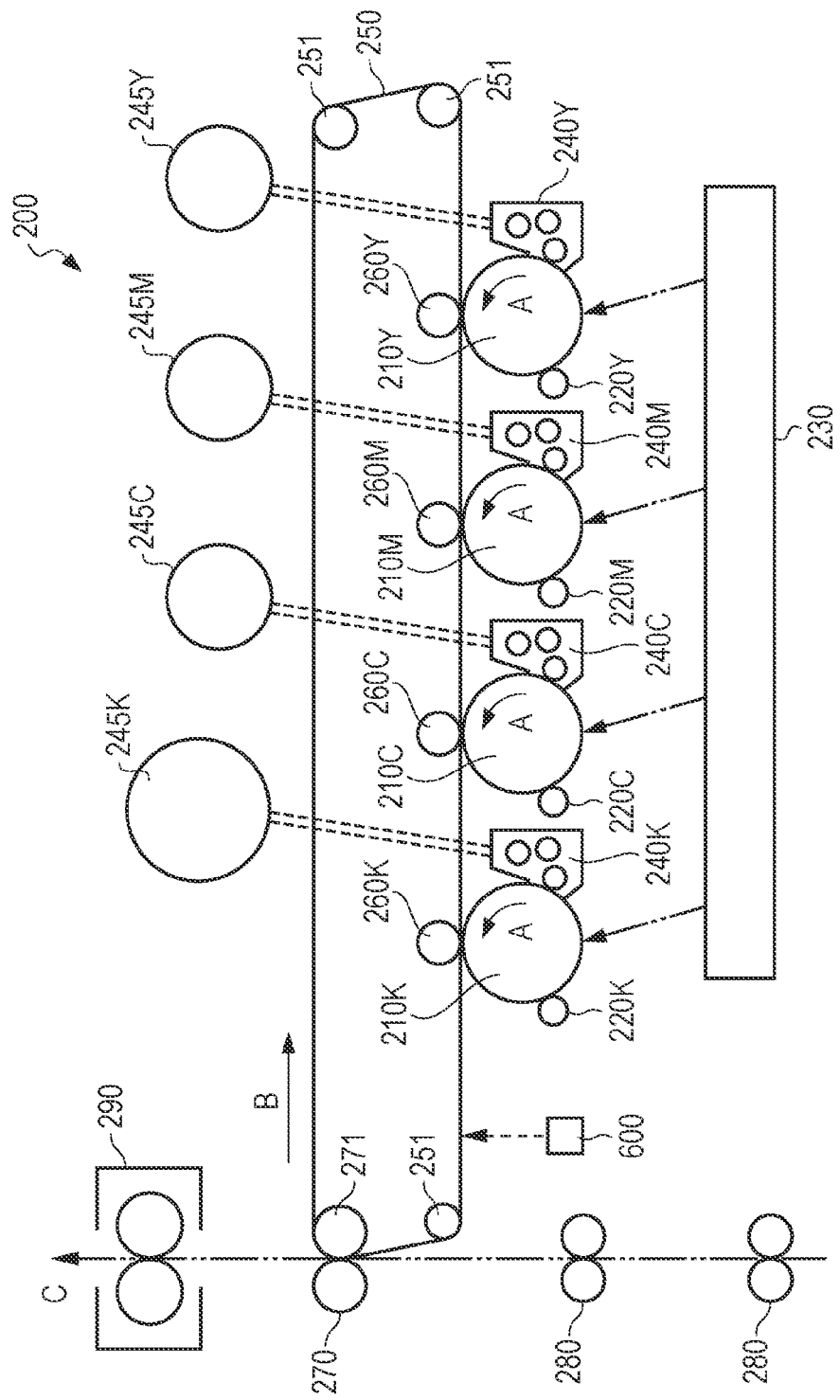
FIG. 2 illustrates the configuration of an image forming unit and a reflection sensor.

FIG. 2 illustrates the configuration of the image forming unit 200 and the reflection sensor 600.

The image forming unit 200 includes, as shown in FIG. 2, photoconductor drums 210Y, 210M, 210C, and 210K, charging devices 220Y, 220M, 220C, and 220K, an exposure device 230, developing devices 240Y, 240M, 240C, and 240K, toner boxes 245Y, 245M, 245C, and 245K, an intermediate transfer belt 250, plural rotation rollers 251, first transfer rollers 260Y, 260M, 260C, and 260K, a second transfer roller 270, a backup roller 271, plural transport rollers 280, and a fixing device 290. A recording medium is transported through the image forming unit 200 in a direction indicated by the broken arrow C in FIG. 2, and images are formed on the recording medium.

In the image forming unit 200, alphabetical characters (Y, M, C, and K) appended to reference numerals refer to associated colors used for forming images. Components having the same reference numeral and different alphabetical characters have the same configuration although the positions thereof and toners used in the components are different. The components having the same configuration are indicated only by a reference numeral while omitting alphabetical characters appended thereto unless it is necessary to distinguish the individual components.

The photoconductor drums 210 are cylindrical members having multilayered photoconductive films on the surface. While the photoconductor drums 210 are in contact with the intermediate transfer belt 250, they are rotated in a direction indicated by the arrow A in FIG. 2 about the center of the cylinder in accordance with the movement of the intermediate transfer belt 250. The charging devices 220 charge the photoconductive films of the photoconductor drums 210 at a predetermined potential. The exposure device 230 irradiates (exposes) the charged photoconductor drums 210 with light and thereby forms electrostatic latent images on the photoconductor drums 220 in accordance with the amount of exposure light. The exposure intensity and exposure positions of the exposure device 230 are controlled by the controller 100. The scanning direction of exposure light emitted from the exposure device 230 is the same as the axial direction (perpendicular to the plane of the drawing in FIG. 2) of the photoconductor drums 210. In this exemplary embodiment, the axial direction of the photoconductor drums 210 is set as the lateral direction of the image forming unit 200, and is hereinafter simply referred to as the "lateral direction". The direction orthogonal to the lateral direction is set as the process direction of the image forming unit 200, and is simply referred to as the "process direction".

The developing devices 240 contain developer made from a mixture of toner and carrier which is supplied from the associated toner boxes 245, and develop electrostatic latent images formed on the photoconductor drums 210 by using toner. The developing devices 240 generate a potential difference between the developing devices 240 and the photoconductor drums 210 and thereby move the charged toner onto the surfaces of the photoconductor drums 210.

The intermediate transfer belt 250 is an endless belt member which is made of a material that regularly reflects light applied to the surface of the intermediate transfer belt 250. The intermediate transfer belt 250 is a medium that rotates in a direction indicated by the arrow B in FIG. 2 while being in contact with the rotation rollers 251, the first transfer rollers 260, and the backup roller 271. The rotation rollers 251 are cylindrical members that support the movement of the intermediate transfer belt 250 and are rotated about the center of the cylinder. There are two types of rotation rollers 251. One type is that the rotation rollers 251 are driven by a driver and rotate by themselves, and the other type is that the rotation rollers 251 are rotated in accordance with the movement of the intermediate transfer belt 250. The first transfer rollers 260 are cylindrical members that face the associated photoconductor drums 210 with the intermediate transfer belt 250 therebetween. The first transfer rollers 260 generate a potential difference between the first transfer rollers 260 and the associated photoconductor drums 210 and thereby transfer toner adhering on the surfaces of the photoconductor drums 210 onto the surface of the intermediate transfer belt 250. The second transfer roller 270 is a cylindrical member that faces the backup roller 271 with the intermediate transfer belt 250 therebetween. The second transfer roller 270 generates a potential difference between the second transfer roller 270 and the backup roller 271 and thereby transfers, at this transfer position, toner on the surface of the intermediate transfer belt 250 onto the surface of a recording medium. The transport rollers 280 are cylindrical members that transport a recording medium, such as paper, to a position at which the second transfer roller 270 transfers toner to paper, and transport paper on which toner is transferred to the fixing device 290. The fixing device 290 heats and pressurizes the recording medium on which toner is transferred and thereby fixes the toner on the recording medium.

The reflection sensor 600 is disposed at a position at which it reads the surface of the intermediate transfer belt 250, on the downstream side of an area where the photoconductor drum 210K and the first transfer roller 260K face each other and on the upstream side of an area where the second transfer roller 270 and the backup roller 271 face each other, with respect to the transfer direction (process direction) of the intermediate transfer belt 250. That is, the reflection sensor 600 reads the surface of the intermediate transfer belt 250 on which an image has been transferred.

Practically, two reflection sensors 600 are provided for the image forming apparatus 10 so that they each read either side of the intermediate transfer belt 250 in the lateral direction. However, since the two reflection sensors 600 function in the same manner in the image forming apparatus 10, only one reflection sensor 600 will be described below.

Figure 3:
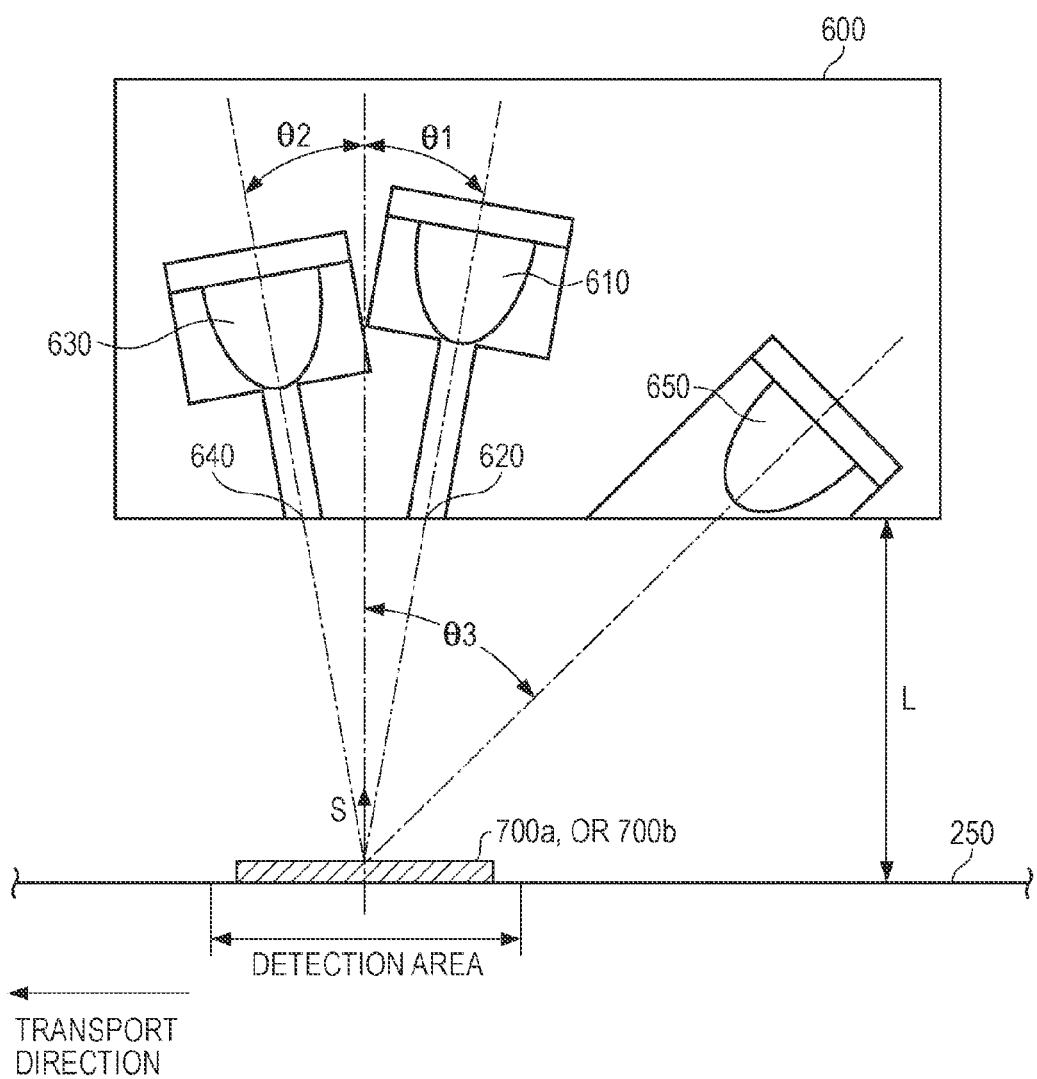
FIG. 3 illustrates the configuration of a reflection sensor.
Figure 4:
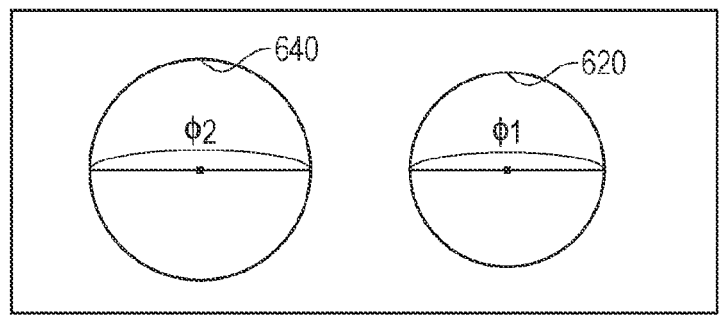
FIG. 4 is a schematic view illustrating a first aperture and a second aperture.

FIG. 3 illustrates the configuration of the reflection sensor 600. The reflection sensor 600 includes, as shown in FIG. 3, a light emitting unit 610, a first aperture 620, a first light receiver 630, a second aperture 640, and a second light receiver 650. FIG. 4 is a schematic view illustrating the first aperture 620 and the second aperture 640 of the reflection sensor 600, as viewed from the intermediate transfer belt 250 in the direction of the normal line S with respect to the surface of the intermediate transfer belt 250.

The light emitting unit 610 is an example of a light emitting unit of an exemplary embodiment of the invention. The light emitting unit 610 is a light emitting diode (LED) in this exemplary embodiment. The light emitting unit 610 emits light toward an area where the position detection image 700a is formed on the surface of the intermediate transfer belt 250. The position detection image 700a is a general term for position detection pattern images of plural colors (examples of a first detection image of an exemplary embodiment of the invention) used for detecting amounts of misregistration among the position detection pattern images. The light emitting unit 610 may also emit light toward an area where the density detection image 700b (an example of a second detection image of an exemplary embodiment of the invention) is formed on the surface of the intermediate transfer belt 250. The density detection image 700b is used for detecting a density deviation from a predetermined reference density.

The first aperture 620 is an example of a first light restricting member/configuration of an exemplary embodiment of the invention. The first aperture 620 is disposed between the light emitting unit 610 and the intermediate transfer belt 250, and serves as a diaphragm that restricts light emitted from the light emitting unit 610. The first aperture 620 allows light which is emitted from the light emitting unit 610 and which is to be applied to the area in which the position detection image 700a or the density detection image 700b is formed to pass through the first aperture 620. Hereinafter, the area which is irradiated with light passing through the first aperture 620 and which is detected by the reflection sensor 600 is referred to as a "detection area". As shown in FIG. 4, the first aperture 620 has a circular opening, and the aperture diameter (also called the "light emitting aperture diameter") φ1 is 1.07 mm.

The light emitting unit 610 and the first aperture 620 are disposed so that the angle θ1 between the normal line S and the axial direction of light applied to the intermediate transfer belt 250 is 10 degrees.

The first light receiver 630 is an example of a light receiver of an exemplary embodiment of the invention. The first light receiver 630 includes a phototransistor. The first light receiver 630 is disposed on an optical path of light which is regularly reflected by the detection area irradiated with light passing through the first aperture 620. The first light receiver 630 receives light reflected by the detection area and outputs a signal representing the amount of received light. More specifically, the first light receiver 630 outputs a photocurrent, which becomes larger as the amount of received light is greater. The amount of received light is measured in accordance with the magnitude of the photocurrent.

The reflection sensor 600 converts an electric signal, which is a photocurrent, output from the first light receiver 630 into a voltage (V) by using a current (A)-to-voltage (V) conversion circuit (not shown), and outputs the voltage to the controller 10.

The second aperture 640 is an example of a second light restricting member/configuration of an exemplary embodiment of the invention. The second aperture 640 is disposed between the first light receiver 630 and the intermediate transfer belt 250. The second light receiver 640 is disposed on an optical path of light which is regularly reflected by the detection area irradiated with light passing through the first aperture 620. The second aperture 640 is a diaphragm which restricts light which has been reflected by the detection area and which is to be received by the first light receiver 630. As shown in FIG. 4, the second aperture 640 has a circular opening, and the aperture diameter (also called the "light emitting aperture diameter") φ2 is 1.12 mm. The first receiver 630 and the second aperture 640 are disposed so that the angle θ2 between the normal line S and the axial direction of light reflected by the detection area is 10 degrees. The second aperture 640 allows light regularly reflected by the detection area to pass through the second aperture 640, and blocks diffusion reflection light so as to reduce the amount of diffusion reflection light received by the first light receiver 630.

The aperture diameters φ1 and φ2 of the first and second apertures 620 and 640, respectively, are set so that the precision in detecting amounts of misregistration is improved. The basis for setting the aperture diameters φ1 and φ2 and the function of the set aperture diameters φ1 and φ2 will be discussed later.

The first and second apertures 620 and 640 are disposed at positions at which they are separated from the detection area by a distance L of 8.0 mm with respect to the normal line S. The position of the reflection sensor 600 in the image forming apparatus 10 is corrected so that the first light receiver 630 can receive the maximum (peak) amount of light reflected by the detection area. That is, the reflection sensor 600 is an optical system whose optical-axis focal point is 8.0 mm. To satisfy such conditions, various factors, such as the position of the light emitting unit 610 and the position and the aperture diameter of the first aperture 620, are corrected.

The second light receiver 650 has the same configuration as that of the first light receiver 630. The second light receiver 650 is disposed at a position at which it receives diffusion reflection light from the detection area irradiated with light passing through the first aperture 620. The second light receiver 650 receives light reflected by the detection area and outputs a signal representing the amount of reflected light. The second light receiver 650 is disposed so that the angle θ3 between the normal line S and the axial direction of the light reflected by the detection area is 50 degrees.

The position detection image 700a and the density detection image 700b will now be discussed below.

Figure 5:
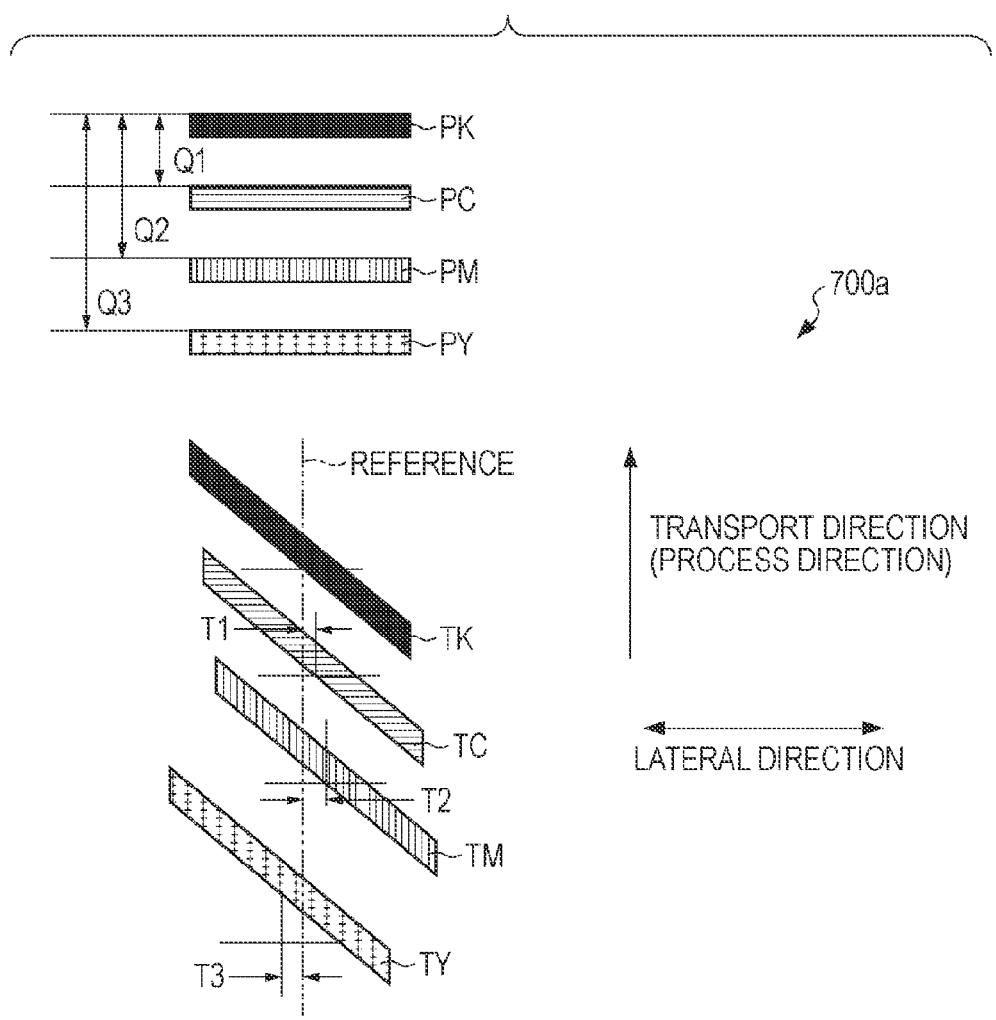
FIG. 5 illustrates a position detection image.

FIG. 5 illustrates the position detection image 700a. In FIG. 5, the horizontal direction corresponds to the lateral direction, and the vertical direction corresponds to the process direction (the direction from the bottom to the top in FIG. 5 is the transport direction of the intermediate transfer belt 250).

As shown in FIG. 5, the position detection image 700a is constituted of a black parallel pattern PK and a black tilt pattern (45°) TK, a cyan parallel pattern PC and a cyan tilt pattern (45°) TC, a magenta parallel pattern PM and a magenta tilt pattern (45°) TM, and a yellow parallel pattern PY and a yellow tilt pattern (45°) TY, those patterns being aligned along the transport direction (process direction) of the intermediate transfer belt 250. The parallel patterns are segment images longitudinally extending in the lateral direction. The tilt patterns are segment images which are tilted so that the angle between the tilt patterns and each of the lateral direction and the process direction is 45 degrees.

Each of the parallel patterns and the tilt patterns is an example of position detection images of individual colors of an exemplary embodiment of the invention.

Figure 6:
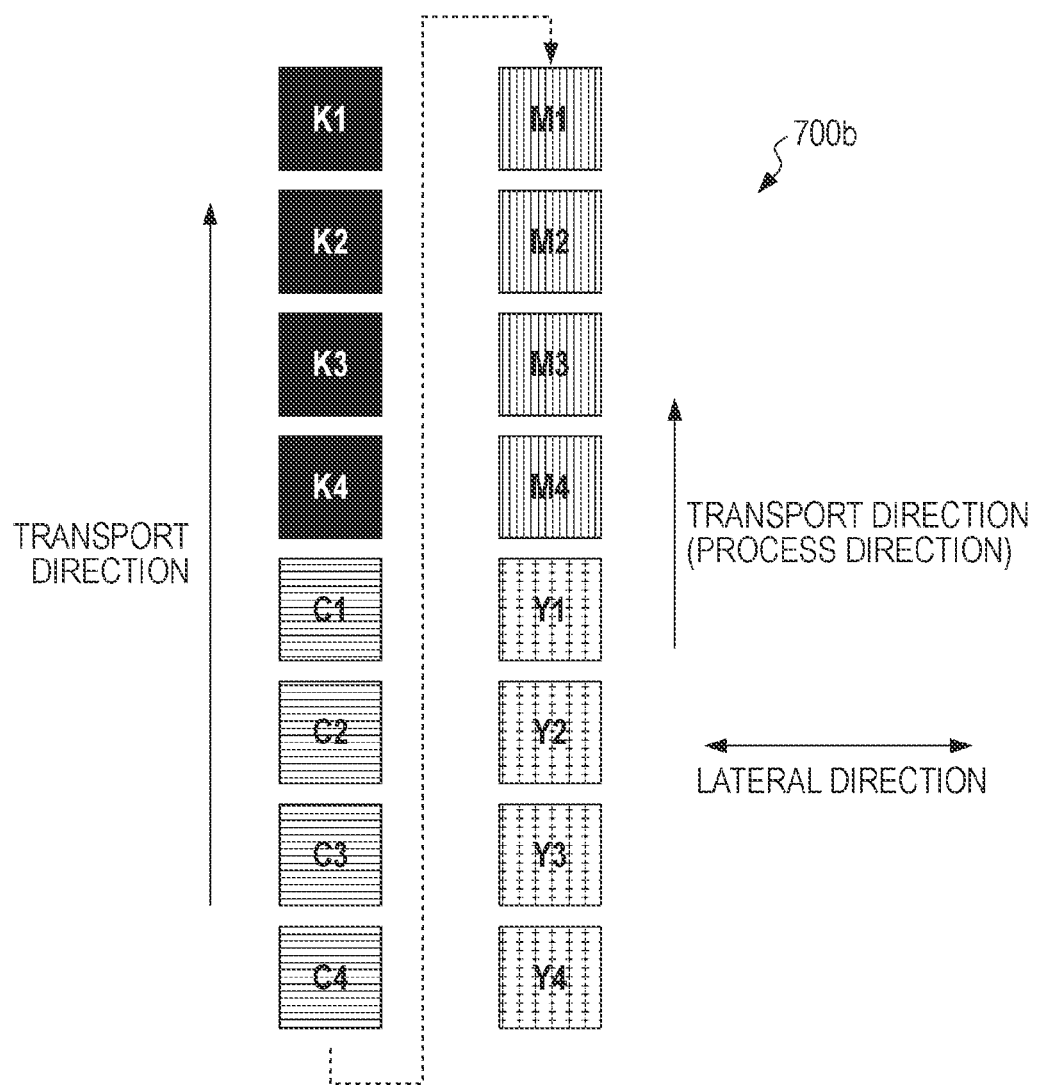
FIG. 6 illustrates a density detection image.

FIG. 6 illustrates the density detection image 700b.

The density detection image 700b includes, as shown in FIG. 6, plural square pattern images formed with a uniform density by using toner of one of the Y, M, C, and K colors (so-called primary colors). The density detection image 700b is constituted of plural pattern images aligned along the transport direction (process direction) of the intermediate transfer belt 250. In this exemplary embodiment, the density indicates the coverage ratio of toner to the background (more specifically, the surface of the intermediate transfer belt 250) per unit area. When the coverage ratio is 0%, the intermediate transfer belt 250 is colorless (background color), and when the coverage ratio is 100%, the intermediate transfer belt 250 has a so-called solid color. In FIG. 6, the alphabetical characters indicate the colors of the pattern images, and the numbers followed by the alphabetical characters indicate the density levels of the pattern images. In this example, as the number is smaller, the density level is higher. For example, a pattern image with the number "1" has a density level of 100%, a pattern image with the number "2" has a density level of 75%, a pattern image with the number "3" has a density level of 50%, and a pattern image with the number "4" has a density level of 25%.

The position detection image 700a and the density detection image 700b shown in FIGS. 5 and 6, respectively, are examples only. The position detection image 700a may be modified in accordance with a detection method for detecting amounts of misregistration. For example, the position detection image 700a may be constituted of ladder patterns, as those disclosed in Japanese Unexamined Patent Application Publication No. 2010-232896, or inverted-V-shaped charts or cross-shaped charts, as those disclosed in Japanese Unexamined Patent Application Publication No. 2011-107524. The density detection image 700b may include pattern images with density levels different from those described above, or may include secondary or tertiary pattern images.

Figure 7:
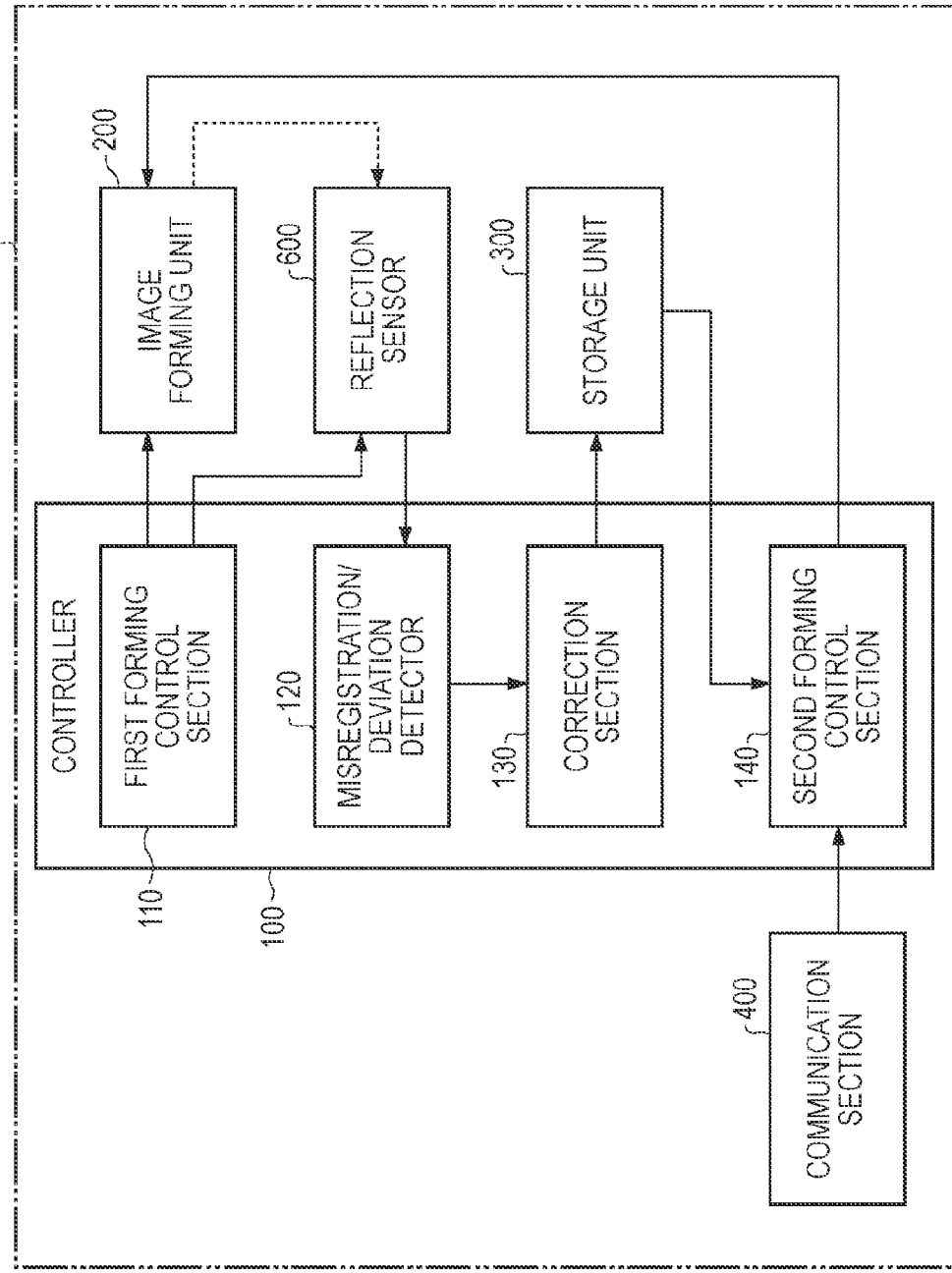
FIG. 7 is a block diagram illustrating an example of the functional configuration of a controller of an image forming apparatus.

FIG. 7 is a block diagram illustrating an example of the functional configuration of the controller 100. The controller 100 implements functions corresponding to a first forming control section 110, a misregistration/deviation detector 120, a correction section 130, a second forming control section 140 shown in FIG. 7 by executing a program.

The first forming control section 110 controls the image forming unit 200 so that the intermediate transfer belt 250 forms the position detection image 700a and the density detection image 700b on the basis of image data stored in the storage unit 300. Additionally, in accordance with a time at which the position detection image 700a and the density detection image 700b are formed, the first forming control section 110 operates the reflection sensor 600 so that the reflection sensor 600 reads the position detection image 700a and the density detection image 700b.

The misregistration/deviation detector 120 is an example of a misregistration/deviation detector of an exemplary embodiment of the invention. The misregistration/deviation detector 120 detects amounts of misregistration and density deviations on the basis of a signal output from the reflection sensor 600. In this example, the misregistration/deviation detector 120 detects amounts of misregistration of individual colors and a density deviation of the K color on the basis of an output signal (i.e., regular reflection light components) from the first light receiver 630, and detects density deviations of the Y, M, and C colors on the basis of an output signal (i.e., diffusion reflection light components) from the second light receiver 650. A detection method for detecting amounts of misregistration by the misregistration/deviation detector 120 will be discussed below.

The misregistration/deviation detector 120 calculates time intervals at which the yellow, magenta, and cyan parallel patterns PY, PM, and PC pass on the reflection sensor 600 with respect to the black parallel pattern PK. As shown in FIG. 5, the misregistration/deviation detector 120 calculates a time interval Q1 between the time when the black parallel pattern PK passes on the reflection sensor 600 and the time when the cyan parallel pattern PC passes on the reflection sensor 600, a time interval Q2 between the time when the black parallel pattern PK passes on the reflection sensor 600 and the time when the magenta parallel pattern PM passes on the reflection sensor 600, and a time interval Q3 between the time when the black parallel pattern PK passes on the reflection sensor 600 and the time when the yellow parallel pattern PY passes on the reflection sensor 600. Then, on the basis of the calculated time intervals Q1, Q2, and Q3, the misregistration/deviation detector 120 calculates amounts of misregistration of the cyan, magenta, and yellow parallel patterns PC, PM, and PY, respectively, with respect to the black parallel pattern PK in the process direction. The misregistration/deviation detector 120 also detects amounts of misregistration of the yellow, magenta, and cyan tilt patterns TY, TM, and TC with respect to the black tilt pattern TK in the lateral direction. As shown in FIG. 5, the misregistration/deviation detector 120 detects an amount of misregistration T1 between the black tilt pattern TK and the cyan tilt pattern TC, an amount of misregistration T2 between the black tilt pattern TK and the magenta tilt pattern TM, and an amount of misregistration T3 between the black tilt pattern TK and the yellow tilt pattern TY.

The correction section 130 is an example of an correction section of an exemplary embodiment of the invention. The correction section 130 corrects the position of an image which is to be formed by the image forming unit 200 on the basis of amounts of misregistration detected by the misregistration/deviation detector 120. The correction section 130 also corrects the density of an image which is to be formed by the image forming unit 200 on the basis of density deviations detected by the misregistration/deviation detector 120.

The second forming control section 140 causes the image forming unit 200 to form an image on a recording medium on the basis of image data used for performing image forming processing obtained from the storage unit 300 or the communication unit 400. The second forming control section 140 causes the image forming unit 200 to form an image with corrected positions and density levels by using correction amounts calculated by the correction section 130.

An operation performed by the image forming apparatus 10 will be described below.

FIG. 8 is a flowchart illustrating process steps executed by the controller 100 of the image forming apparatus 10.

In step S1, the controller 100 determines whether setup processing including detection of amounts of misregistration and density deviations is to be performed. Setup processing is performed when predetermined conditions in the image forming apparatus 10 are satisfied, i.e., when it is likely that there may be a change in misregistration or density deviation, such as power ON of the image forming apparatus 10, supply of toner or replacement of components, a sudden change in environments, such as the temperature or humidity, at predetermined regular intervals (e.g. once a day), etc.

If the controller 100 determines in step S1 that setup processing is to be performed, the process proceeds to step S2. In step S2, the controller 100 controls the image forming unit 200 so that the image forming unit 200 forms the position detection image 700a and the density detection image 700b (see FIGS. 5 and 6, respectively) on the surface of the intermediate transfer belt 250. Then, in step S3, the controller 100 causes the reflection sensor 600 to read, as a detection area, the surface of the intermediate transfer belt 250 on which the position detection image 700a and the density detection image 700b are formed. Then, in step S4, the controller 100 detects amounts of misregistration and density deviations on the basis of signals output from the first light receiver 630 and the second light receiver 650 of the reflection sensor 600. More specifically, the controller 100 detects amounts of misregistration on the basis of an output signal from the first light receiver 630. The controller 100 also detects a density deviation of a K pattern image of the density detection image 700b on the basis of the signal (i.e., regular reflection light components) output from the first light receiver 630, and detects density deviations of Y, M, and C pattern images of the density detection image 700b on the basis of the signal (i.e., diffusion reflection light components) output from the second light receiver 650. The controller 100 detects amounts of misregistration by comparing the positions of the Y, M, C, and K pattern images of the position detection image 700a read by the reflection sensor 600 with a target position, and also detects density deviations by comparing the density levels of the Y, M, C, and K pattern images of the density detection image 700b read by the reflection sensor 600 with a target density.

Then, in step S5, the controller 100 calculates correction amounts so that the positions of the pattern images of the position detection image 700a approximate to the target position and so that the density levels of the pattern images of the density detection image 700b approximate to the target density. The controller 100 then stores the calculated correction amounts in the storage unit 300. The controller 100 calculates correction amounts for decreasing (ideally eliminating) misregistration by adjusting the start timing of exposure in the exposure device 230 or by correcting image data. The controller 100 also calculates correction amounts for decreasing (ideally eliminating) density deviations by adjusting at least one of the charging potential in the charging devices 220, the exposure intensity in the exposure device 230, the developing bias in the developing devices 240, and the amounts of toner supplied from the toner boxes 245.

The controller 100 may update the correction amounts stored in the storage unit 300 every time setup processing is performed so that the latest correction amounts can be always utilized. The setup processing of this exemplary embodiment includes steps S1 through S5 described above.

The controller 100 determines in step S6 whether image forming processing is to be performed. If the controller 100 determines in step S6 that image forming processing is to be performed since image data used for image formation has been received by the communication unit 400 or an instruction to perform image forming processing has been given through an operation performed on the UI 500, the process proceeds to step S7. In step S7, image forming processing is performed so that images which have been corrected for their positions and density levels on the basis of correction amounts stored in the storage unit 300 are formed on a recording medium by the image forming unit 200.

In step S8, the controller 100 determines whether the image forming apparatus 10 has been turned OFF. If it is determined in step S8 that the image forming apparatus 10 has not been turned OFF (the result of step S8 is NO), the process returns to step S1, and the above-described steps are repeated. If it is determined that the image forming apparatus 10 has been turned OFF (the result of step S8 is YES), the processing is completed.

If the controller 100 determines in step S1 that setup processing is not to be performed (the result of step S1 is NO), the process proceeds to step S6. If the controller determines in step S6 that image forming processing is not to be performed (the result of step S6 is NO), the process proceeds to step S8. That is, as long as the image forming apparatus 10 is ON, the controller 100 is in the standby state in which setup processing or image forming processing is to be performed.

For the sake of simple description, the image forming apparatus 10 detects both misregistration and density deviations. However, the conditions for performing misregistration may be different from those for performing density deviations. In this case, the image forming apparatus 10 detects only one of amounts of misregistration and density deviations and updates the associated correction amounts.

The configuration and the operation of the image forming apparatus 10 have been discussed above.

The present inventors have found that the aperture diameters of the first and second apertures 620 and 640 satisfy a specific relationship in order to improve detection precision in detecting misregistration by using the reflection sensor 600. The aperture diameters of the above-described first and second apertures 620 and 640 satisfy this specific relationship. The process for discovering such a specific relationship by the inventors will be discussed below.

The reason why special adjustments are necessary for the aperture diameters of the first and second apertures 620 and 640 is as follows.

Figure 9A:
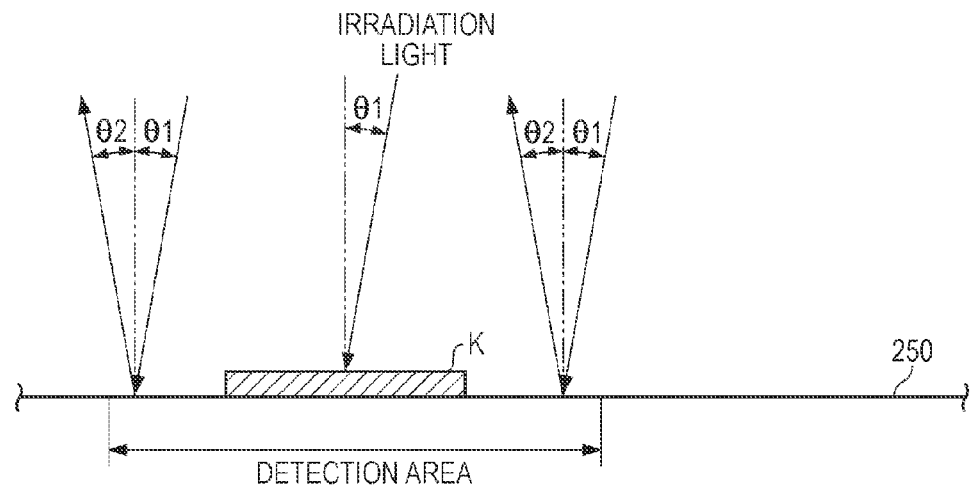
FIGS. 9A and 9B illustrate optical paths when a reflection sensor reads images of individual colors.
Figure 9B:
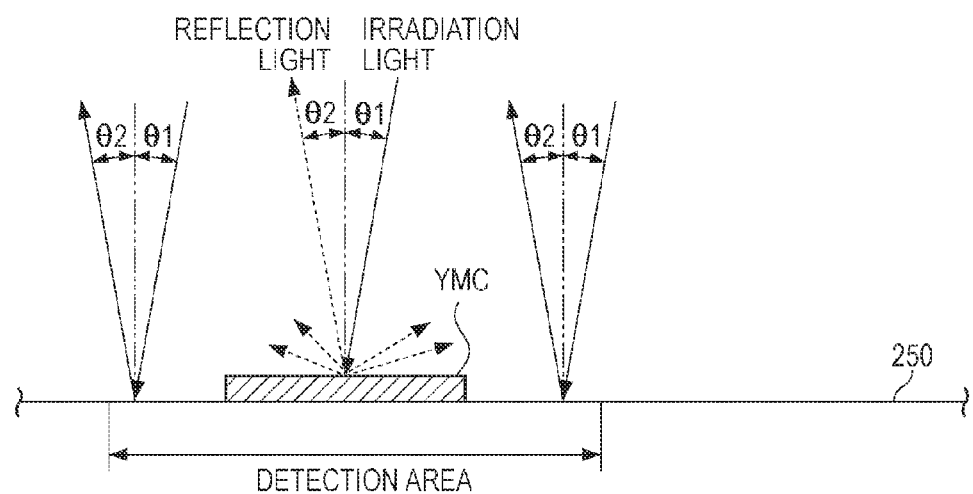

FIG. 9A illustrates optical paths when the reflection sensor 600 reads a K pattern image. FIG. 9B illustrates optical paths when the reflection sensor 600 reads Y, M, and C pattern images.

As shown in FIG. 9A, when light is incident on a K pattern image formed on the intermediate transfer belt 250 at an incident angle of θ1, light applied to an area where the K pattern image is formed is almost completely absorbed, and light applied to an area where the K pattern image is not formed is regularly reflected (as regular reflection light) by that area at an angle of θ2, which is the same as θ1. In contrast, as shown in FIG. 9B, when light is incident on Y, M, and C pattern images, light is reflected by an area where the Y, M, and C pattern images are formed at an angle of θ2, not only as regular reflection light, but also as diffusion reflection light. This generates a difference (contrast ratio) between the density of the Y, M, and C pattern images and the density of the K pattern image even though the density of the Y, M, and C pattern images is originally the same as that of the K pattern image, thereby leading to a difference between the detection precision in detecting the K pattern image and that in detecting the Y, M, and C pattern images by using the reflection sensor 600.

In view of this background, in order to decrease the difference between the detection precision in the K pattern image and that in the Y, M, and C pattern images, it is necessary to inhibit the reflection sensor 600 from receiving diffusion reflection light.

Figure 10:
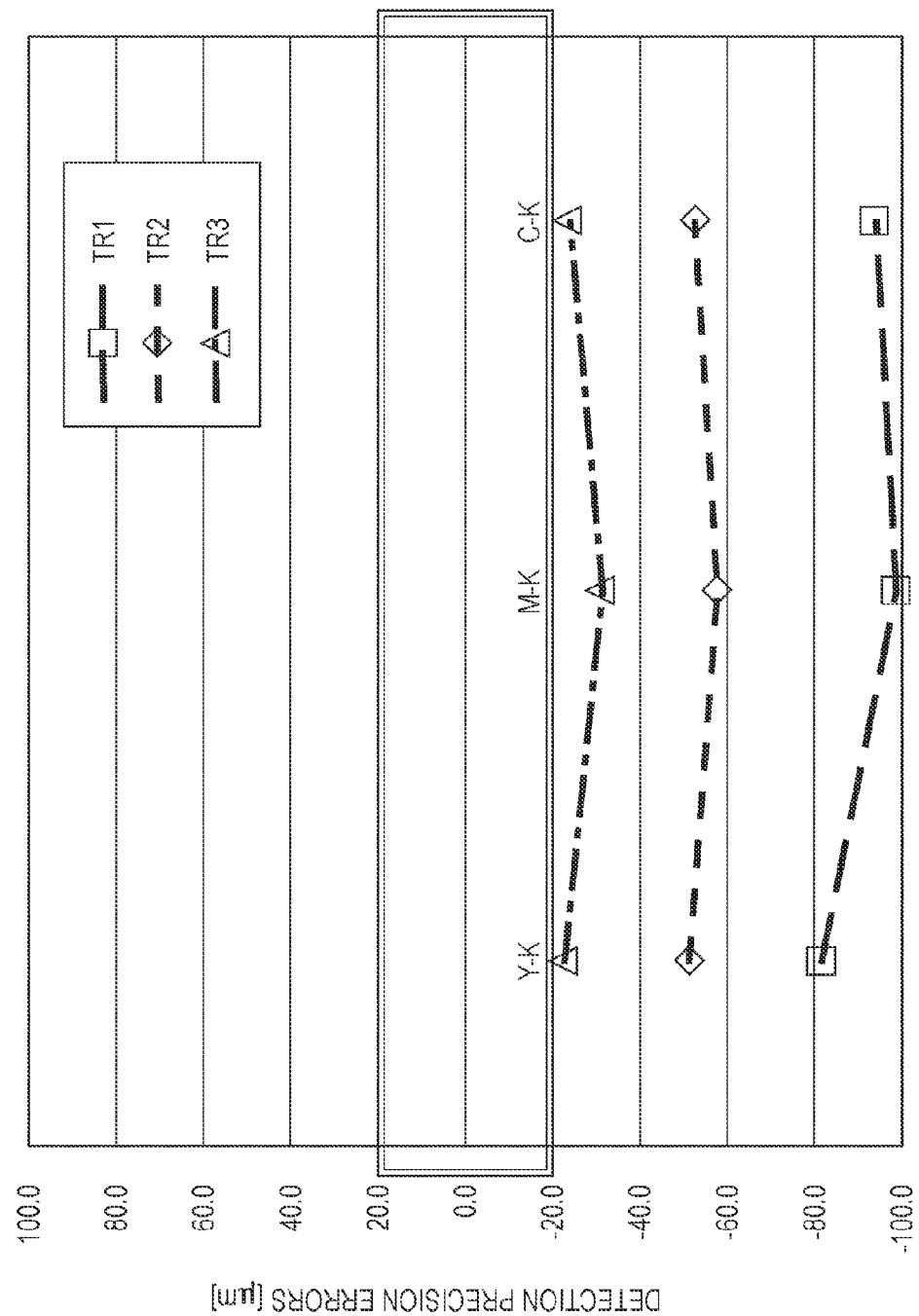
FIG. 10 illustrates relationships between a detection precision error of a K image and detection precision errors of Y, M, and C images.

After measuring detection precision errors between the K pattern image and the Y, M, and C pattern images by the present inventors, the measuring results shown in FIG. 10 are obtained. In FIG. 10, the detection precision errors are represented by relative misregistration between positions at which the K pattern image is detected and positions at which the Y, M, and C pattern images are detected (so-called "color difference"), and are indicated by micrometers (μm). In the following description, the detection precision errors indicated by the sign "+" mean that, in the lateral direction or in the process direction, the Y, M, and C pattern images are displaced from the K pattern image in one side, and the detection precision errors indicated by the sign "−" mean that, in the lateral direction or in the process direction, the Y, M, and C pattern images are displaced from the K pattern image in the other side. In FIG. 10, "Y-K" indicates the detection precision errors between the Y and K pattern images, "M-K" indicates the detection precision errors between the M and K pattern images, and "C-K" indicates the detection precision errors between the C and K pattern images.

FIG. 10 shows that the detection precision error increases in the order of "C-K", "M-K", and "Y-K", however, this is an example only.

As shown in FIG. 10, as a result of examining detection precision errors by using three reflection sensors indicated by TR1, TR2, and TR3, the detection precision error exceeds 20 μm regardless of which reflection sensor is used. The light emitting aperture and the light receiving aperture of the TR1 reflection sensor are 0.9 mm and 1.6 mm, respectively. The light emitting aperture and the light receiving aperture of the TR2 reflection sensor are both 2.4 mm. The light emitting aperture and the light receiving aperture of the TR3 reflection sensor are 2.4 mm and 1.5 mm, respectively.

Thus, the present inventors have set the target value of the detection precision errors to 20 μm and have performed verification tests so that the detection precision errors are restricted within the target value. The inventors have first verified the relationship between detection precision errors and each of the aperture diameter φ1 of the first aperture 620, the aperture diameter φ2 of the second aperture 640, and the value obtained by dividing the aperture diameter φ2 of the second aperture 640 by the aperture diameter φ1 of the first aperture 620 (hereinafter such a value is referred to as the "light emitting and receiving aperture ratio").

Figure 11:
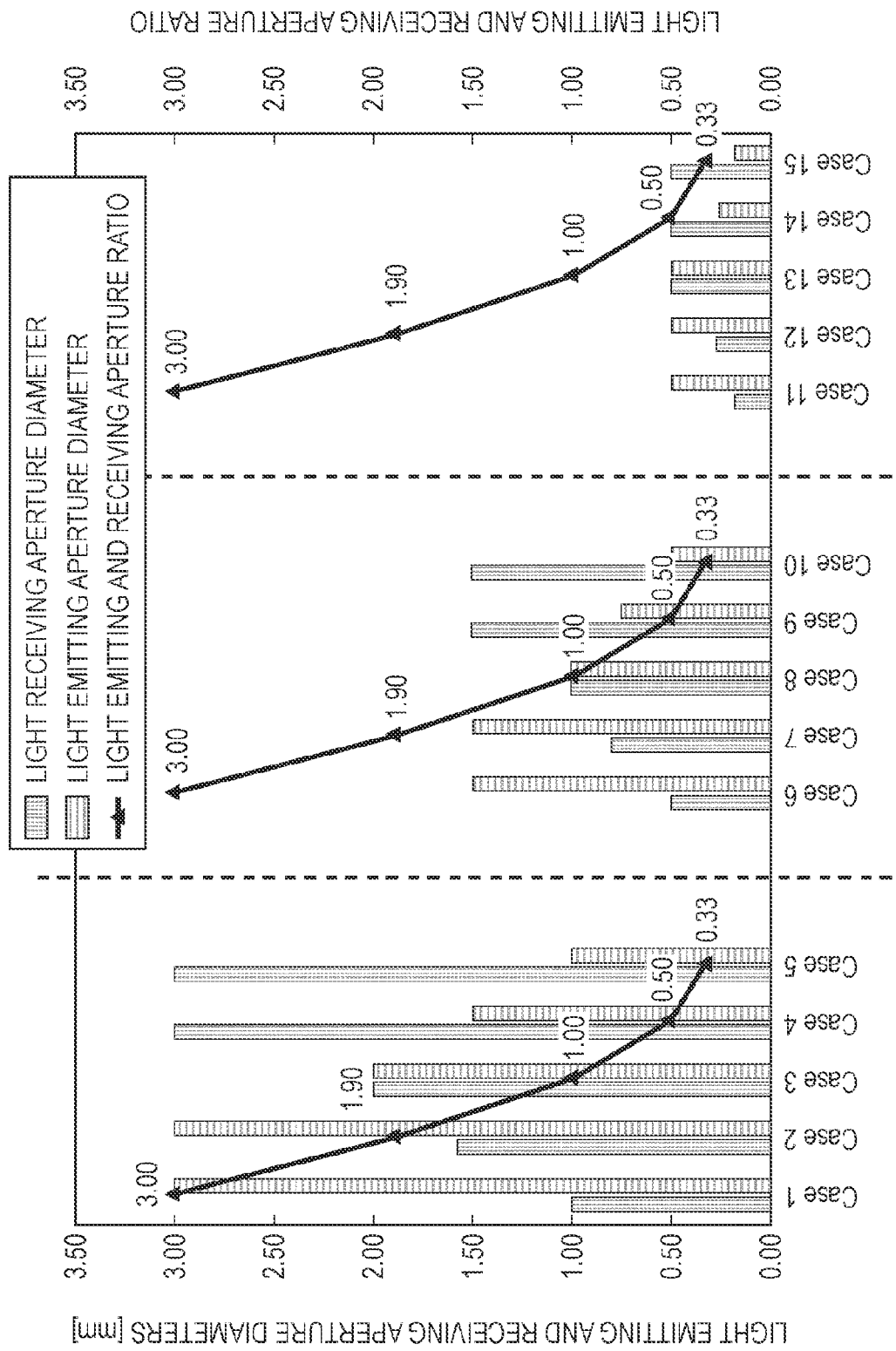
FIG. 11 illustrates reflection sensors used for verifying detection precision errors.

FIG. 11 illustrates reflection sensors of Case 1 through Case 15 used for checking detection precision errors. The structure of those reflection sensors is the same as that of the reflection sensor 600, but aperture conditions are different from those of the reflection sensor 600. The light emitting aperture and the light receiving aperture may collectively be referred to as "light emitting and receiving apertures".

FIG. 11 shows the following verification results. Concerning the reflection sensors of Case 1 through Case 5, the aperture diameter of at least one of the light emitting and receiving apertures exceeds 1.5 mm. Concerning the reflection sensors of Case 6 through Case 10, the aperture diameter of at least one of the light emitting and receiving apertures ranges from 0.5 to 1.5 mm. Concerning the reflection sensors of Case 11 through Case 15, the aperture diameter of at least one of the light emitting and receiving apertures is smaller than 0.5 mm. The light emitting and receiving aperture ratio of the reflection sensors of Cases 1, 6, and 11 is 3.00. The light emitting and receiving aperture ratio of the reflection sensors of Cases 2, 7, and 12 is 1.90. The light emitting and receiving aperture ratio of the reflection sensors of Cases 3, 8, and 13 is 1.00. The light emitting and receiving aperture ratio of the reflection sensors of Cases 4, 9, and 14 is 0.50. The light emitting and receiving aperture ratio of the reflection sensors of Cases 5, 10, and 15 is 0.33.

Figure 12:
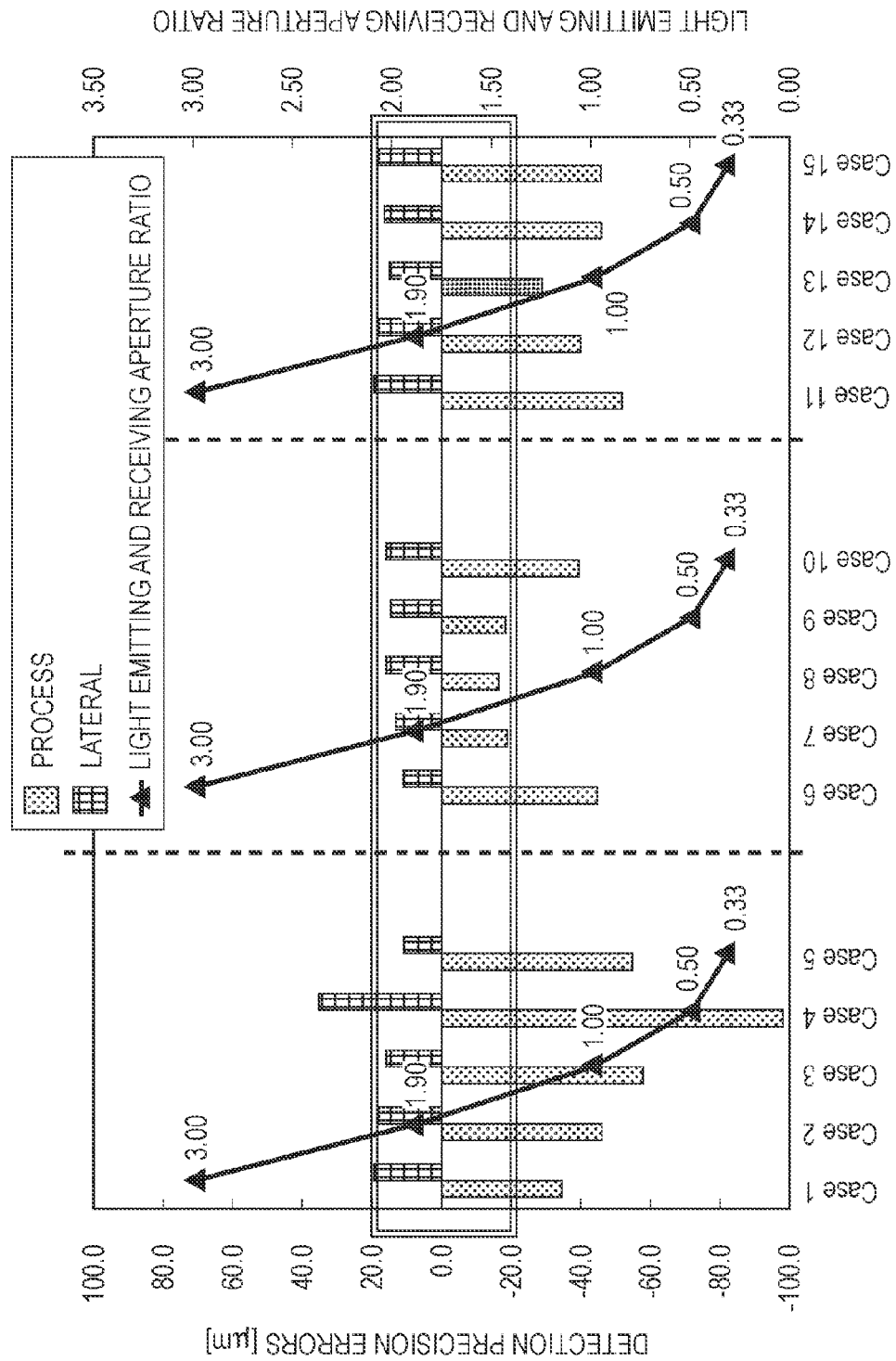
FIG. 12 illustrates relationships of the aperture diameters and the light emitting and receiving aperture ratio to detection precision errors.

FIG. 12 illustrates relationships between results of measuring detection precision errors and the aperture diameters and the light emitting and receiving aperture ratio of each of the reflection sensors of Case 1 through Case 15. The results of measuring detection precision errors shown in FIG. 12 (and FIGS. 13 through 15) indicate the maximum value of the "Y-K", "M-K", and "C-K" detection precision errors.

FIG. 12 shows the following verification results. Concerning the reflection sensors of Case 1 through Case 5 in which the aperture diameter of at least one of the light emitting and receiving apertures exceeds 1.5 mm, the detection precision error in at least one of the lateral direction and the process direction exceeds ±20 μm, which is the target value.

Concerning the reflection sensors of Case 6 and Case 10 in which the aperture diameter of at least one of the light emitting and receiving apertures ranges from 0.5 to 1.5 mm, the detection precision error in the process direction exceeds ±20 μm, and concerning the reflection sensors of Case 7, Case, 8, and Case 9, the detection precision error in the process direction is within ±20 μm. Concerning the reflection sensor of Case 7, the light emitting aperture diameter, the light receiving aperture diameter, and the light emitting and receiving aperture ratio are 1.50 mm, 0.80 mm, and 1.90, respectively. Concerning the reflection sensor of Case 8, the light emitting aperture diameter, the light receiving aperture diameter, and the light emitting and receiving aperture ratio are 1.00 mm, 1.00 mm, and 1.00, respectively. Concerning the reflection sensor of Case 9, the light emitting aperture diameter, the light receiving aperture diameter, and the light emitting and receiving aperture ratio are 0.75 mm, 1.50 mm, and 0.50, respectively.

Concerning the reflection sensors of Case 11 through Case 15 in which the aperture diameter of at least one of the light emitting and receiving apertures is lower than 0.5 mm, the detection precision error in at least one of the lateral direction and the process direction exceeds ±20 μm.

The above-described verification results reveal that, concerning the reflection sensors of Case 1 through Case 5 in which the aperture diameter of at least one of the light emitting and receiving apertures exceeds 1.5 mm, the detection precision error exceeds the target value. This may originate from the following reason. A large light emitting aperture diameter makes the detection area large, thereby making it easier to generate diffusion reflection light. Or, a large light receiving aperture diameter makes it easier to receive diffusion reflection light from the detection area. Regardless of whichever reason it is, as the aperture diameter of at least one of the light emitting and receiving apertures increases, regular reflection sensors more easily receive diffusion reflection light, thereby relatively increasing the influence of diffusion reflection light on the detection precision in detecting amounts of misregistration.

The above-described verification results reveal that, within the range in which the aperture diameters of the light emitting and receiving apertures range from 0.5 mm to 1.5 mm and when the light emitting and receiving aperture ratio is 0.5 or greater and smaller than 1.9, there are certain ranges of aperture diameter and the light emitting and receiving aperture ratio in which the detection precision error may be within ±20 μm.

Assuming that the aperture diameters of the light emitting and receiving apertures are 1.5 mm or smaller, when the light emitting and receiving aperture ratio is 0.5 or greater and smaller than 1.9, the aperture diameters of the light emitting and receiving apertures are inevitably restricted to 0.8 mm or greater. This range hereinafter indicates that the light emitting and receiving aperture ratio is 0.5 or greater and smaller than 1.9 and the aperture diameters of the light emitting and receiving apertures are 1.5 mm or smaller. Then, it is verified whether the detection precision error will be within ±20 μm, which is the target value, in this entire range.

Concerning a reflection sensor attached to an image forming apparatus, the position at which the reflection sensor is attached to the image forming apparatus may be slightly displaced from a correct position. Additionally, because of vibration generated in the image forming apparatus, the reflection sensor is also vibrated, and the angle at which the reflection sensor is attached to the image forming apparatus may be slightly displaced from a correct angle. In addition to the reasons regarding the reflection sensor, because of the occurrence of flapping of the intermediate transfer belt 250, the detection precision of the reflection sensor may be decreased. Concerning the reflection sensors of Case 11 through Case 15 in which the aperture diameters of both of the light emitting and receiving apertures are smaller than 0.5 mm, large detection precision errors may be originated from the following reasons. In those sensors, the detection areas are smaller than those of the other reflection sensors, and thus, robustness in the image forming apparatus may be decreased because of the above-described reasons, i.e., resistance to various changeable factors of the image forming apparatus is decreased. Accordingly, the present inventors have verified in detail the relationships between the aperture diameters of light emitting and receiving apertures and increased detection precision errors originated from decreased robustness.

Figure 13:
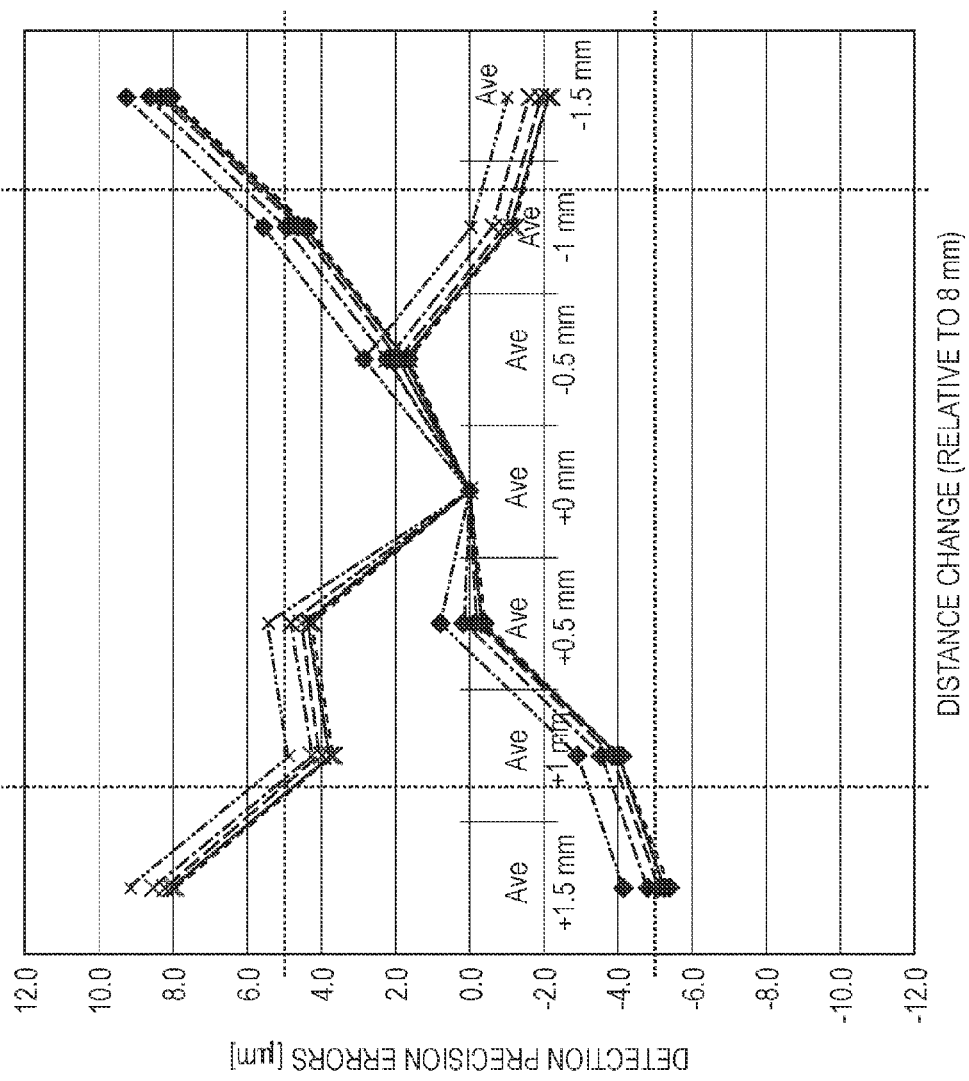
FIG. 13 illustrates the relationships between a change in the distance from each of reflection sensors to a detection area and a detection precision error.

FIG. 13 illustrates the relationships between a change in the distance L from the light receiving aperture to a detection area and a detection precision error. In the graph of FIG. 13, the distance L is set to be 8 mm. FIG. 13 illustrates detection precision errors when the aperture diameters of the light emitting and receiving apertures are 3.00 mm, 1.90 mm, 1.00 mm, 0.50 mm, and 0.33 mm, and when the averages of changes in the distance L are 0.00 mm, ±0.50 mm, ±1.00 mm, and ±1.50 mm. The detection precision errors include a detection precision error in the lateral direction (indicated by "Lat" in FIG. 13) and a detection precision error in the process direction (indicated by "Pro" in FIG. 13).

FIG. 13 shows that, regardless of the size of the aperture diameters of the light emitting and receiving apertures, as a change in the distance L increases, the detection precision error increases. In particular, as the aperture diameter decreases, this tendency becomes more noticeable. In the image forming apparatus provided with a reflection sensor, when the distance L is changed in excess of about 1.0 mm to 1.5 mm, the detection precision error exceeds 5 μm only because of a change in the distance L. This makes it difficult to restrict the detection precision error within ±20 μm, which is the target value. Such a decrease in the detection precision may originate from the following reason. A change in the distance L changes the position of the focal point of the optical axis, which reduces the amount of received regular reflection light from the detection area to be detected by the sensor.

Figure 14:
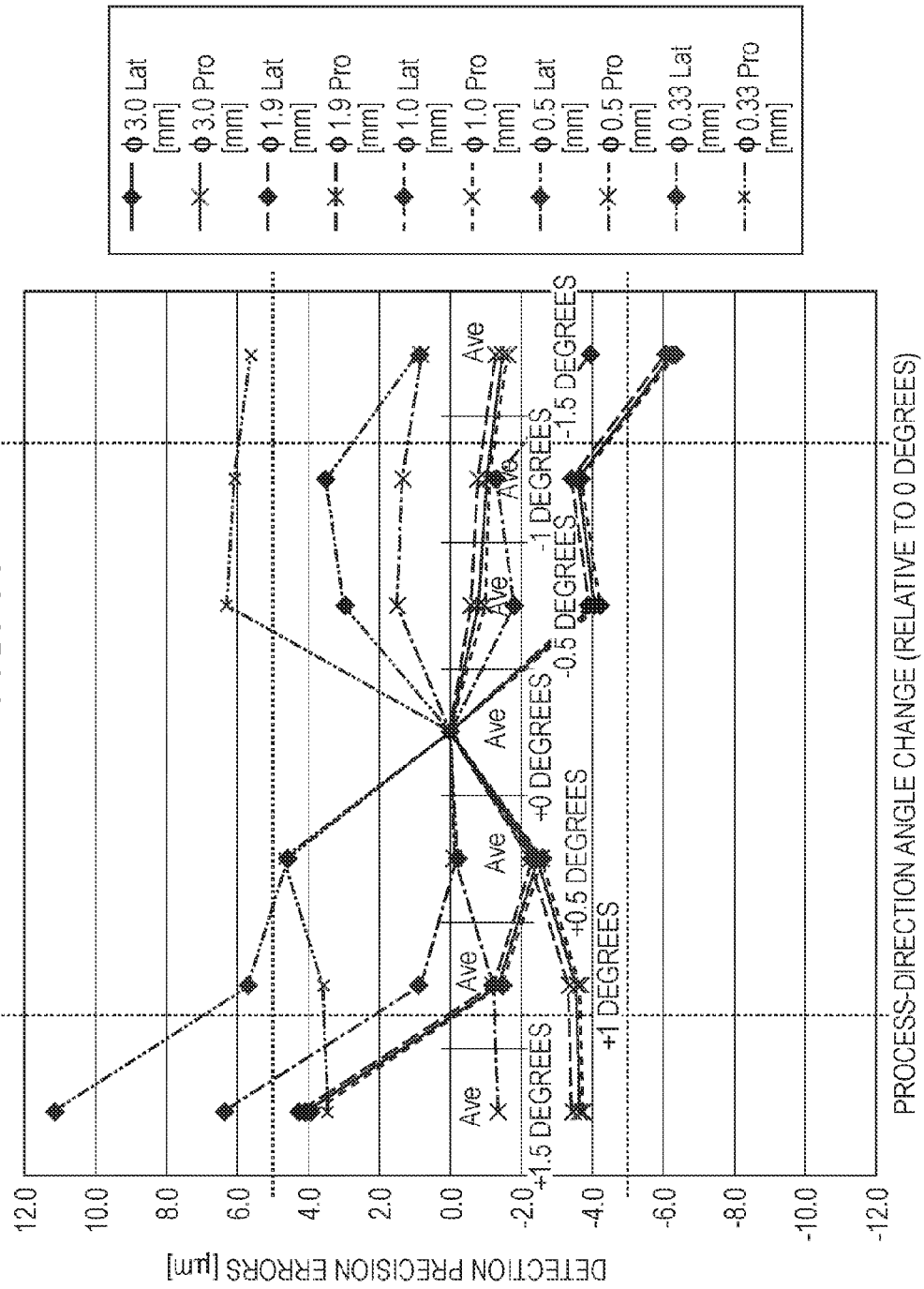
FIG. 14 illustrates the relationships between a process-direction angle change of each of reflection sensors and a detection precision error.
Figure 15:
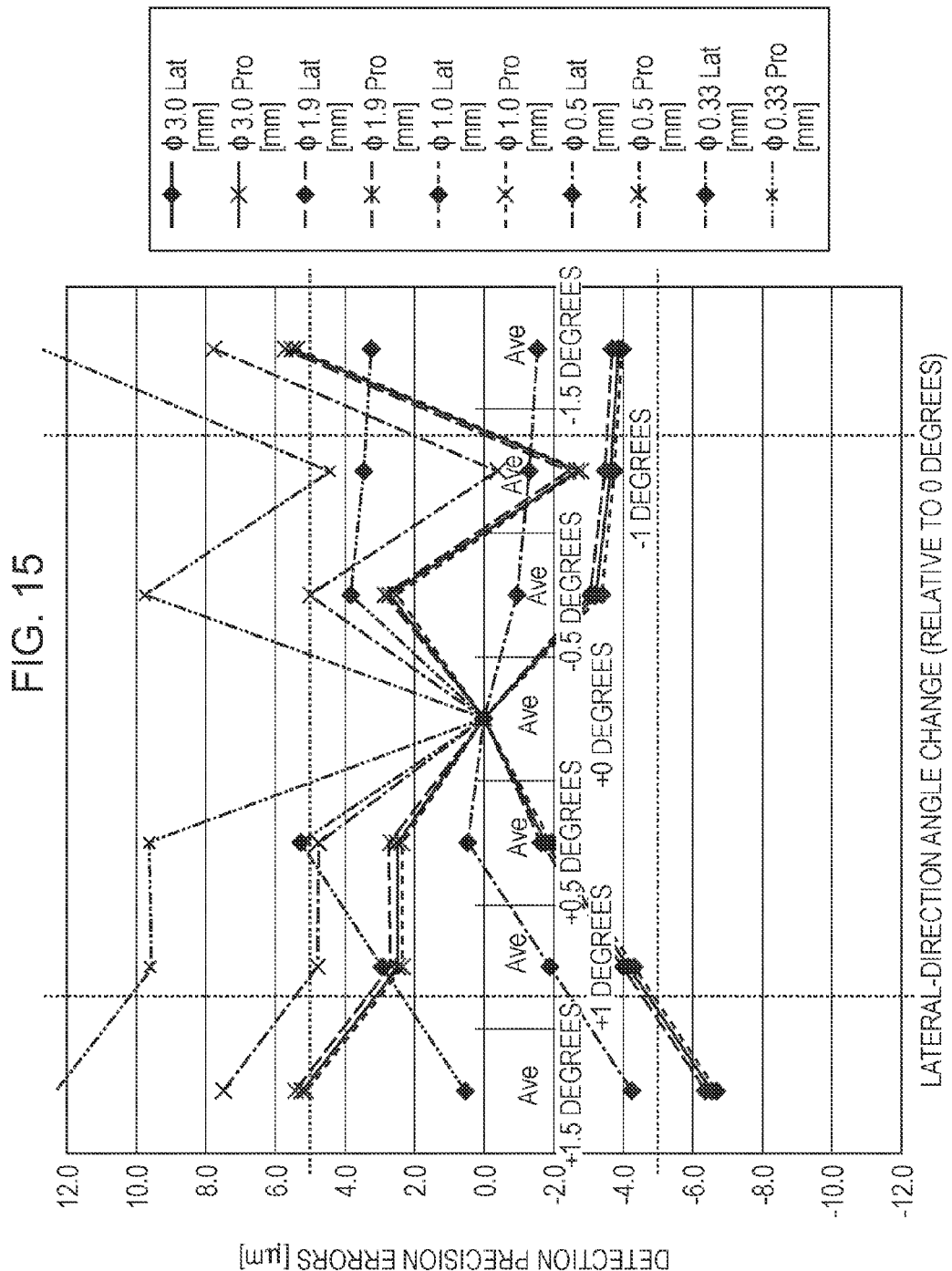
FIG. 15 illustrates the relationships between a lateral-direction angle change of each of reflection sensors and a detection precision error.

FIG. 14 illustrates the relationships between a change in the angle of a reflection sensor in the process direction (such a change is referred to as the "process-direction angle change") and a detection precision error. FIG. 15 illustrates the relationships between a change in the angle of a reflection sensor in the lateral direction (such a change is referred to as the "lateral-direction angle change") and a detection precision error. FIGS. 14 and 15 illustrate detection precision errors when the aperture diameters of the light emitting and receiving apertures are 3.00 mm, 1.90 mm, 1.00 mm, 0.50 mm, and 0.33 mm and when the averages of changes in the angle are 0 degrees, ±0.50 degrees, ±1.00 degrees, and ±1.50 degrees. The detection precision errors include a detection precision error in the lateral direction (indicated by "Lat" in FIGS. 14 and 15) and a detection precision error in the process direction (indicated by "Pro" in FIGS. 14 and 15).

FIGS. 14 and 15 show that, regardless of the size of the aperture diameters of the light emitting and receiving apertures, as a change in the angle increases, the detection precision error increases. In particular, as the aperture diameter decreases, this tendency becomes more noticeable. In the image forming apparatus provided with a reflection sensor, when the angle is changed in excess of about 1.0 to 1.5 degrees, the detection precision error exceeds 5 μm only because of a change in the angle. This makes it difficult to restrict the detection precision error within ±20 μm, which is the target value. Such a decrease in the detection precision may originate from the following reason. A change in the angle caused by vibration of the sensor decreases the amount of received regular reflection light from the detection area to be detected by the sensor.

The above-described results of measuring detection precision errors in accordance with a change in the distance and a change in the angle show that, if the aperture diameters are too small, detection precision decreases because of reduced robustness in the image forming apparatus.

By summarizing the above-described verification results, if the aperture diameters of the light emitting and receiving apertures are somewhat large, detection precision errors increase mainly because of the influence of diffusion reflection light, and if the aperture diameters of the light emitting and receiving apertures are somewhat small, detection precision errors increase mainly because reduced robustness in the image forming apparatus. The fact that detection precision errors in the reflection sensors of Case 7, Case 8, and Case 9 are within the ±20 μm, which is the target value, may be because of the following reason. Because of the relationship between the aperture diameters of the light emitting and receiving apertures, an increase in detection precision errors can be suppressed while being free from the influence of diffusion reflection light and reduced robustness in the image forming apparatus. It is thus concluded that detection precision errors can be restricted within the ±20 μm if the aperture diameters of the light emitting and receiving apertures and the light emitting and receiving aperture ratio are those within the ranges defined in Case 7, Case 8, and Case 9.

Figure 16:
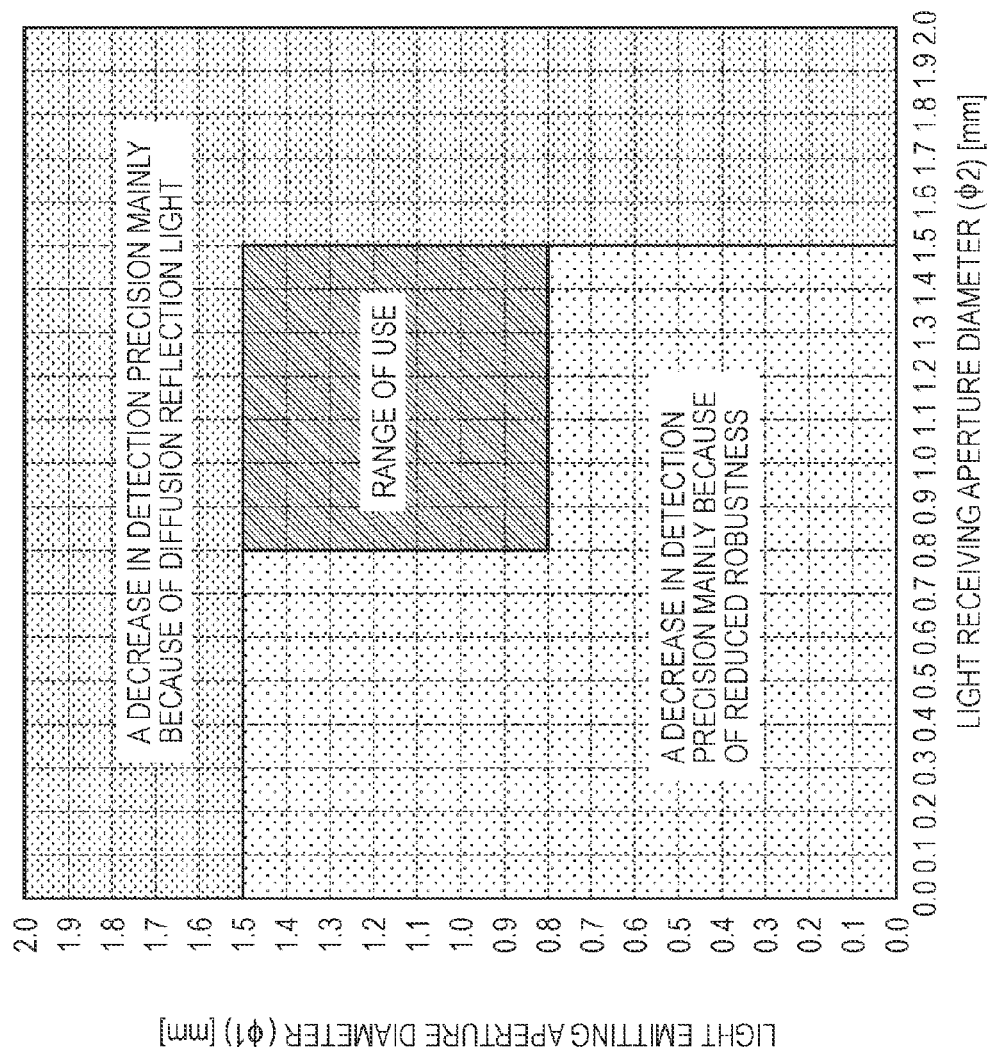
FIG. 16 illustrates the conditions of apertures so as to implement a target value of restrict detection precision errors.

FIG. 16 illustrates the relationships determined by the above-described verification results, i.e., the relationships between detection precision and the aperture diameters of the light emitting and receiving apertures and the light emitting and receiving aperture ratio in reflection sensors. In FIG. 16, the vertical axis indicates the size of the light emitting aperture diameter ($\phi$1), and the horizontal axis indicates the size of the light receiving aperture diameter ($\phi$2).

The range indicated by the "range of use" in FIG. 16 is a range in which the light emitting and receiving aperture ratio is 0.5 or greater and smaller than 1.9 and the light emitting aperture diameter ($\phi$1) and the light receiving aperture diameter ($\phi$2) are 1.5 mm or smaller. In the range in which at least one of the light emitting aperture diameter and the light receiving aperture diameter exceeds 1.5 mm, the detection precision decreases mainly because of diffusion reflection light. In the range in which at least one of the light emitting aperture diameter and the light receiving aperture diameter is smaller than 0.8 mm and the light emitting and receiving aperture ratio is less than 0.5 or exceeds 1.9, the detection precision decreases mainly because of reduced robustness in the image forming apparatus.

The above-described verification results show that the detection precision errors are restricted within ±20 μm if the aperture diameters $\phi$1 and $\phi$2 of the first and second apertures 620 and 640, respectively, are set within the "range of use" shown in FIG. 16. The aperture diameters $\phi$1 and $\phi$2 may be changed within the "range of use" shown in FIG. 16.

As the aperture diameters $\phi$1 and $\phi$2 are farther away from the range in which detection precision may be decreased due to diffusion reflection light and from the range in which detection precision may be decreased due to reduced robustness in the image forming apparatus, and approach closer to the center of the "range of use", a decrease in the detection precision may become even smaller. Accordingly, the aperture diameters of the first and second apertures 620 and 640 may be from 0.9 mm to 1.4 mm, and more preferably, 1.0 mm to 1.3 mm.

According to the above-described exemplary embodiment, a technique is provided for detecting amounts of misregistration of images by using the reflection sensor 600 that receives regular reflection light, and a decrease in detection precision caused by diffusion reflection light and reduced robustness in an image forming apparatus is suppressed. Additionally, in the image forming apparatus 10, since the reflection sensor 600 includes the second light receiver 650 that receives diffusion reflection light, only one sensor, i.e., the reflection sensor 600, is sufficient to detect amounts of misregistration and density deviations. Accordingly, it is not necessary that a sensor for detecting amounts of misregistration (e.g., a marks-on-belt (MOB) sensor) and a sensor for detecting density deviations (e.g., an auto density control (ADC) sensor) be separately provided in the image forming apparatus 10. This makes it possible to reduce the number of components installed in the image forming apparatus 10.

Concerning the detection precision in density deviations by using the reflection sensor 600, density deviations are corrected by using a reference board disclosed in Japanese Unexamined Patent Application Publication No. 5-322760, thereby securing detection precision when the reflection sensor 600 is installed in the image forming apparatus 10. Thus, by the use of the reflection sensor 600, the detection precision in detecting both of amounts of misregistration and density deviations can be secured when the reflection sensor 600 is installed in the image forming apparatus 10.

MODIFIED EXAMPLES

The present invention may be carried out in an exemplary embodiment different from the above-described embodiment. Alternatively, the following modified examples may be combined.

In the above-described embodiment, the reflection sensor 600 has both a function of detecting amounts of misregistration and a function of detecting density deviations. However, the reflection sensor 600 may have only a function of detecting amounts of misregistration. That is, even if the reflection sensor 600 does not have the second light receiver 650, a decrease in the detection precision in detecting amounts of misregistration caused by diffusion reflection light and reduced robustness in the image forming apparatus 10 is suppressed. In this case, the reflection sensor 600 has one light emitting unit and one light receiver.

The reflection sensor 600 may have any number of light emitting units and light receivers. Additionally, if the reflection sensor 600 has a configuration for detecting density levels of Y, M, and C colors (e.g., a polarizing device) by using regular reflection light components, it functions as a sensor for detecting amounts of misregistration and density deviations even if it does not have the second light receiver 650.

The amounts of light reflected by a detection area as regular reflection light and as diffusion reflection light are changed in accordance with the distance from the detection area to the reflection sensor 600 with respect to the direction of the normal line S. In the reflection sensor 600, it is preferable that the distance, in the direction of the normal line S with respect to the detection area, between the position of the second aperture 640 at which the first receiver 630 can receive the maximum (peak) amount of light and the position of the second aperture 640 at which the first receiver 630 receives the maximum (peak) amount of light reflected by the detection area as diffusion reflection light is large. Such a distance is referred to as the "inter-peak distance". This is because of the assumption that, as the inter-peak distance is larger, the amount of diffusion reflection light contained in reflection light received by the first light receiver 630 is decreased, thereby contributing to an improvement in the detection precision in detecting amounts of misregistration.

The present inventors have discovered that the setting of the inter-peak distance of 1.0 mm or greater is suitable for improving the detection precision in detecting amounts of misregistration.

Figure 17:
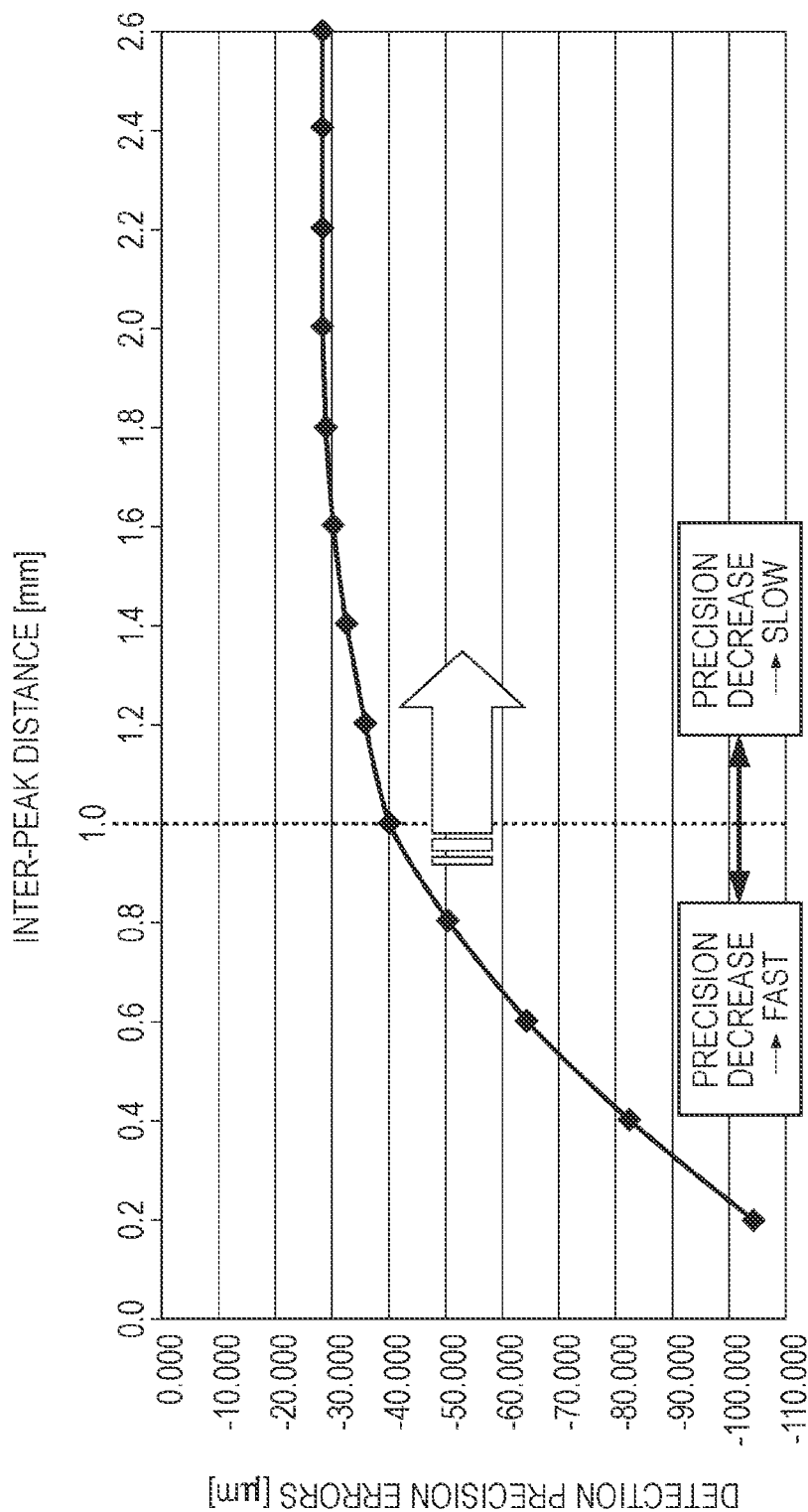
FIG. 17 illustrates the relationship between the inter-peak distance and a detection precision error.

FIG. 17 illustrates the relationship between the inter-peak distance and a detection precision error. In measuring the inter-peak distance and the detection precision error, the aperture diameters of the light emitting and receiving apertures are set to be 3.0 mm.

FIG. 17 shows the following results. When the inter-peak distance is smaller than 1.0 mm, the detection precision error is sharply changed in accordance with a change in the inter-peak distance, and as the inter-peak distance increases, the detection precision error is decreased. In contrast, when the inter-peak distance is 1.0 mm or greater, a decrease in the detection precision error is small, and even if the inter-peak distance is increased, it is difficult to improve detection precision any further. The measuring results reveal that it is preferable that the inter-peak distance is set to be 1.0 mm or greater in terms of an improvement in detection precision by adjusting the inter-peak distance.

In measuring the inter-peak distance, the amount of diffusion reflection light may be measured in any manner. In this case, diffusion reflection light is detected by setting the incident angle to be 10 degrees (=θ1), as in the reflection sensor 600, and by setting the reflection angle to be 0 degrees (=θ2). In detecting diffusion reflection light, the amounts of diffusion reflection light received at the positions with respect to the direction of the normal line S as a result of light being applied to the position detection image 700*a* and being reflected by the position detection image 700*a* are measured. Then, the position at which the amount of diffusion reflection light is maximized is specified. On the basis of such a position, the focal point of the optical axis of the reflection sensor 600 is set so that the inter-peak distance becomes 1.0 mm or greater. In setting the focal point of the optical axis of the reflection sensor 600, various conditions, such as the position of the light emitting unit 610 and the position and the aperture diameter of the first aperture 620, may be set.

The first and second apertures 620 and 640 are apertures (diaphragms) having openings for restricting light. However, they may each have another member, such as a condensing lens, for restricting light.

The first and second apertures 620 and 640 have circular openings. However, the configurations of the first and second apertures 620 and 640 are not particularly restricted, and may be any shape as long as the aperture diameters satisfy the above-described conditions.

In the image forming unit 200, the medium on which the position detection image 700*a* and the density detection image 700*b* are formed is not restricted to the intermediate transfer belt 250. Any medium (e.g., a paper medium) may be used as long as it is made of a material that regularly reflects light applied to the surface of the medium.

The functions implemented by the controller 100 of the image forming apparatus 10 of the above-described embodiment may be realized by one or plural hardware circuits or as a result of executing one or plural programs by using an arithmetic unit, or may be realized by a combination thereof.

In the above-described embodiment, an image forming apparatus has been discussed by way of example. Alternatively, only a detection apparatus for detecting amounts of misregistration and density deviations by using the reflection sensor 600 may be configured as a detachable option apparatus. More specifically, such a detection apparatus includes the reflection sensor 600 and implements a function corresponding to the misregistration/deviation detector 120. The detection apparatus detects amounts of misregistration and density deviations on the basis of the position detection image 700*a* and the density detection image 700*b*, respectively, formed by an image forming apparatus, which is an external apparatus.

The foregoing description of the exemplary embodiment and modified examples of the present invention have been provided for the purposes of illustration and description. It is not intended to be exhaustive or to limit the invention to the precise forms disclosed. Obviously, many modifications and variations will be apparent to practitioners skilled in the art. The embodiment and modified examples were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A reflection sensor comprising:
a light emitting unit that emits light to an area of an image forming apparatus where first detection images of a plurality of colors are formed, the first detection images being used for detecting amounts of misregistration among the first detection images:
a first light restricting member/configuration that restricts light emitted from the light emitting unit:
a light receiver that is disposed in an optical path of regular reflection light generated as a result of light passing through the first light restricting member/configuration and applied to the area being reflected by the area, and that receives light reflected by the area and outputs a signal representing an amount of received light; and
a second light restricting member/configuration that is disposed in the optical path of the regular reflection light and that restricts light to be received by the light receiver,
wherein a value obtained by dividing a diameter of the first light restricting member/configuration by a diameter of the second light restricting member/configuration ranges from substantially 0.5 to 1.9, and the diameters of the first and second light restricting members/configurations are each 1.5mm or smaller, and
wherein, a distance, in a direction of a normal line with respect to the area, between a position of one of the second light restricting member/configuration, the light emitting unit, and the light receiver at which an amount of light received by the light receiver is maximized and a position of the associated one of the second light restricting member/configuration, the light emitting unit, and the light receiver at which an amount of diffusion reflection light generated as a result of light being reflected by the area is maximized is substantially 1.0 mm or greater.

2. An image forming apparatus comprising:
a reflection sensor including
a light emitting unit that emits light to an area of an image forming apparatus where first detection images of a plurality of colors are formed, the first detection images being used for detecting amounts of misregistration among the first detection images,
a first light restricting member/configuration that restricts light emitted from the light emitting unit,
a light receiver that is disposed in an optical path of regular reflection light generated as a result of light passing through the first light restricting member/configuration and applied to the area being reflected by the area, and that receives light reflected by the area and outputs a signal representing an amount of received light, and
a second light restricting member/configuration that is disposed in the optical path of the regular reflection light and that restricts light to be received by the light receiver,
wherein a value obtained by dividing a diameter of the first light restricting member/configuration by a diameter of the second light restricting member/configuration ranges from substantially 0.5 to 1.9, and the diameters of the first and second light restricting members/configurations are each 1.5 mm or smaller, and
wherein a distance, in a direction of a normal line with respect to the area, between a position of one of the second light restricting member/configuration, the light emitting unit, and the light receiver at which an amount of light received by the light receiver is maximized and a position of the associated one of the second light restricting member/configuration, the light emitting unit, and the light receiver at which an amount of diffusion reflection light generated as a result of light being reflected by the area is maximized is substantially 1.0 mm or greater;
an image forming unit that forms the first detection images and an image represented by image data;
a misregistration/deviation detector that detects the amounts of misregistration among the first detection images on the basis of the signal output from the light receiver; and
a correction unit that corrects a position of an image to be formed by the image forming unit in accordance with the image data, on the basis of the amounts of misregistration detected by the misregistration/deviation detector.

3. The image forming apparatus according to claim 2, wherein:
the image forming unit forms second detection images used for detecting density deviations of the second detection images from a predetermined density;
the reflection sensor applies light to an area of the image forming unit where the second detection images are formed, receives light reflected by the area, and outputs a signal representing the amount of light reflected by the area;
the misregistration/deviation detector detects the density deviations on the basis of the signal representing the amount of light reflected by the area where the second detection images are formed; and
the correction unit corrects a density of the image to be formed by the image forming unit in accordance with the image data, on the basis of the density deviations detected by the misregistration/deviation detector.

4. The image forming apparatus according to claim 2, wherein the reflection sensor is disposed at a position at which an amount of light reflected by the area is maximized, and the second light restricting member/configuration is disposed at a position at which the second light restricting member/configuration is separated from the area by substantially 8.0 mm in a direction of a normal line with respect to the area.

5. The image forming apparatus according to claim 3, wherein the reflection sensor is disposed at a position at which an amount of light reflected by the area is maximized, and the second light restricting member/configuration is disposed at a position at which the second light restricting member/configuration is separated from the area by substantially 8.0 mm in a direction of a normal line with respect to the area.

* * * * *